United States Patent
Waguespack et al.

(10) Patent No.: US 10,988,564 B2
(45) Date of Patent: Apr. 27, 2021

(54) PROCESS FOR PRODUCING DIMETHOXYMETHANE OLIGOMERS

(71) Applicant: Lyondell Chemical Technology, L.P., Houston, TX (US)

(72) Inventors: James N. Waguespack, Spring, TX (US); David S. Mannel, Humble, TX (US); Larry W. Arndt, Humble, TX (US); Ha H. Nguyen, Houston, TX (US); Barbara Kimmich, Houston, TX (US)

(73) Assignee: Lyondell Chemical Technology, L.P., Houston, TX (US)

(*) Notice: Subject to any disclaimer, the term of this patent is extended or adjusted under 35 U.S.C. 154(b) by 66 days.

(21) Appl. No.: 16/297,254

(22) Filed: Mar. 8, 2019

(65) Prior Publication Data

US 2019/0276579 A1 Sep. 12, 2019

Related U.S. Application Data

(60) Provisional application No. 62/641,105, filed on Mar. 9, 2018, provisional application No. 62/641,117, filed on Mar. 9, 2018.

(51) Int. Cl.
| | |
|---|---|
| *C08G 4/00* | (2006.01) |
| *C07C 41/58* | (2006.01) |
| *C07C 41/56* | (2006.01) |
| *B01D 3/14* | (2006.01) |
| *B01D 3/06* | (2006.01) |
| *C07C 43/04* | (2006.01) |
| *C08G 2/24* | (2006.01) |
| *B01L 3/06* | (2006.01) |

(52) U.S. Cl.
CPC ............... *C08G 4/00* (2013.01); *B01D 3/143* (2013.01); *B01D 3/06* (2013.01); *C07C 41/56* (2013.01); *C07C 41/58* (2013.01); *C07C 43/04* (2013.01); *C08G 2/24* (2013.01); *B01D 2257/70* (2013.01)

(58) Field of Classification Search
CPC ........................................ C08G 4/00
USPC ........................................ 528/232
See application file for complete search history.

(56) References Cited

U.S. PATENT DOCUMENTS

| | | |
|---|---|---|
| 2003/0159341 A1 | 8/2003 | Patrini et al. |
| 2008/0207955 A1 | 8/2008 | Stroefer et al. |

FOREIGN PATENT DOCUMENTS

| | | |
|---|---|---|
| EP | 1070755 A1 | 1/2001 |

OTHER PUBLICATIONS

The International Search Report and Written Opinion for PCT/US2019/021415 dated May 9, 2019.

*Primary Examiner* — Shane Fang (57) ABSTRACT

A method of producing dimethoxymethane oligomers (DMMn), the method comprising: reacting a formaldehyde source and dimethoxymethane monomer (DMM1) in the presence of an acidic catalyst to produce a reaction effluent comprising DMMn and unreacted DMM1; and separating, from the reaction effluent, DMM1-2 including unreacted DMM1 and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof, wherein the separating comprises distillation in the presence of at least one alcohol, a distillate fuel, or both.

8 Claims, 3 Drawing Sheets

PROCESS FOR PRODUCING DIMETHOXYMETHANE OLIGOMERS

CROSS-REFERENCE TO RELATED APPLICATIONS

This application claims the benefit of priority to U.S. Provisional Patent Application Nos. 62/641,105 and 62/641,117, each filed on Mar. 9, 2018, which are incorporated herein by reference in their entirety.

TECHNICAL FIELD

This disclosure relates to the production of dimethoxymethane oligomers (DMMn). More specifically, this disclosure relates to the production of DMMn utilizing alcohol blends to react with free formaldehyde, and/or distillate diluent to reduce viscosity and inhibit deposition of heavier oligomers throughout a DMMn distillation system. Still more specifically, this disclosure relates to the production of DMMn utilizing such alcohol blends and/or distillate diluent throughout a two-step DMMn distillation system comprising a first distillation configured to separate a first distillation overhead comprising dimethoxymethane monomer and dimer (e.g., DMM1-2) from a first distillation bottoms comprising DMMn having a chain length n of greater than or equal to 2 (e.g., DMM2+), and a second distillation configured to separate a second distillation overhead comprising DMMn having a chain length n in the range of from 2 to 5 (e.g., DMM2-5) from a second distillation bottoms comprising DMMn having a chain length n of greater than or equal to 5 (e.g., DMM5+).

BACKGROUND

Dimethoxymethane oligomers, also known as poly(oxymethylene) dimethyl ethers and referred to herein as DMMn, may be utilized as components of tailored diesel fuel. The blending of DMMn with distillate fuels may reduce levels of harmful engine exhaust emissions, such as particulates, SOx, NOx and hydrocarbons, and increase levels of cetane of the resulting blended fuel. The absence of sulfur in DMMn may also reduce deleterious effects on combustion engine pollution control equipment. The addition of up to 15% DMMn in diesel oil can reduce the amounts of particulate pollutants released upon combustion by up to 80-90%. The reduction in particulates may also allow for reduction in fuel consumption at low NOx engine operation. DMM monomer (e.g., DMM1), from which DMM oligomer is produced, can be produced from methanol. The abundance in natural gas, future outlook for methanol production, and poor air pollution levels make the production of DMMn and the incorporation thereof into distillate fuels attractive. In addition, since methanol can be derived from gasification of renewable sources, the possibility exists to create a renewable DMMn fuel. The conversion of methanol through formaldehyde to DMMn as an additive of diesel can absorb the methanol production capacity by 50%, and may also provide benefits with respect to economics and environmental protection.

Distillate fuels exhibit characteristics including fungibility, pour point, flash point, cloud point, and cetane number. Fungibility relates to performance in fuel distribution and delivery systems. An indicator of fungibility is the increase of water phase volume when water is contacted with the fuel mixture. The pour point is the temperature at which a liquid becomes semi-solid and loses its flow characteristics. The flash point is the lowest temperature at which vapors of the material will ignite, when given an ignition source. The cloud point is the temperature below which wax in diesel or biowax in biodiesels forms a cloudy appearance. The cetane number is an indicator of the combustion speed of diesel fuel. Fuel compositions comprising distillate fuels and DMMn may be tailored to provide certain fungibility, pour point, flash point, cloud point, and/or cetane number.

Accordingly, a need exists for improved systems and methods for the production of dimethoxymethane oligomers.

SUMMARY

Herein disclosed is a method of producing dimethoxymethane oligomers (DMMn), the method comprising: reacting a formaldehyde source and dimethoxymethane monomer (DMM1) in the presence of an acidic catalyst to produce a reaction effluent comprising DMMn and unreacted DMM1; and separating, from the reaction effluent, DMM1-2 including unreacted DMM1 and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof, wherein the separating comprises distillation in the presence of at least one alcohol, a distillate fuel, or both.

Also disclosed herein is a method of producing dimethoxymethane oligomers (DMMn), the method comprising: producing a feed comprising anhydrous formaldehyde and dimethoxymethane monomer (DMM1) by: reacting aqueous formaldehyde with an alcohol to produce a reaction effluent comprising hemiformal; decomposing the hemiformal to produce the anhydrous formaldehyde; and subjecting the anhydrous formaldehyde to distillation in the presence of DMM1 to separate a heavy stream comprising unreacted alcohol from the feed comprising anhydrous formaldehyde and DMM1; and reacting the feed comprising anhydrous formaldehyde and DMM1 in the presence of an acidic catalyst to produce a reaction effluent comprising DMMn.

Also disclosed herein is a method of producing dimethoxymethane oligomers (DMMn), the method comprising: producing anhydrous formaldehyde by: reacting aqueous formaldehyde with an alcohol to produce a reaction effluent comprising hemiformal; decanting to separate an aqueous phase comprising water from an organic phase comprising the hemiformal; separating water from the organic phase via membrane filtration, another separation, or a combination thereof, to provide an anhydrous hemiformal; and decomposing the anhydrous hemiformal to produce the anhydrous formaldehyde, subjecting the anhydrous formaldehyde to distillation in the presence of dimethoxymethane monomer (DMM1) to separate a heavy stream comprising unreacted alcohol from an anhydrous formaldehyde source containing anhydrous formaldehyde and DMM1, reacting the anhydrous formaldehyde and DMM1 in the presence of an acidic catalyst to produce a reaction effluent comprising DMMn and unreacted DMM1; and separating, from the reaction effluent, DMM1-2 including unreacted DMM1 and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof, wherein the separating, from the reaction effluent, comprises distillation in the presence of at least one alcohol, a distillate fuel, or both.

Herein disclosed is a system for producing dimethoxymethane oligomers (DMMn), the system comprising: a DMMn reactor configured for reacting a formaldehyde source and dimethoxymethane monomer (DMM1) in the presence of an acidic catalyst to produce a reactor effluent comprising DMMn and unreacted DMM1; a first distillation column configured to separate, from the reactor effluent, a first distillation column overhead comprising DMM1-2 including unreacted DMM1 and DMMn having a chain length n equal to 2 (DMM2) from a first distillation column bottoms comprising DMMn wherein n is greater than or equal to 2 (DMM2+); and a second distillation column configured to separate, from the first distillation column bottoms, a second distillation column overhead comprising dimethoxymethane oligomers having a chain length n in the range of from 2-5 (DMM2-5) from a second distillation column bottoms comprising dimethoxymethane oligomers having a chain length n of ≥5 (DMM5+), wherein the first distillation column, the second distillation column, or both are configured for operation in the presence of at least one alcohol, a distillate fuel, or both.

Also disclosed herein is a system for producing dimethoxymethane oligomers (DMMn), the system comprising: a first distillation column configured to separate, from a reactor effluent comprising DMMn, a first distillation column overhead comprising DMM1-2 including dimethoxymethane monomer (DMM1) and DMMn having a chain length n equal to 2 (DMM2) from a first distillation column bottoms comprising DMMn wherein n is greater than or equal to 2 (DMM2+); and a second distillation column configured to separate, from the first distillation column bottoms, a second distillation column overhead comprising dimethoxymethane oligomers having a chain length n in the range of from 2-5 (DMM2-5) from a second distillation column bottoms comprising dimethoxymethane oligomers having a chain length n of ≥5 (DMM5+), wherein the first distillation column, the second distillation column, or both are configured for operation in the presence of at least one alcohol, a distillate fuel, or both.

Also disclosed herein is a method of producing dimethoxymethane oligomers (DMMn), the method comprising: separating, from a DMMn reaction effluent, DMM1-2 comprising unreacted dimethoxymethane monomer (DMM1) and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof, wherein the separating comprises distillation in the presence of at least one alcohol, a distillate fuel, or both.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which:

DETAILED DESCRIPTION

Overview

This disclosure relates to the production of dimethoxymethane oligomers (DMMn). Dimethoxymethane oligomers, also called poly(oxymethylene) dimethyl ethers, have the structure (1):

(1)

where n represents the number of repeating groups in or chain length of the oligomer. Dimethoxymethane oligomers may also be referred to by the abbreviation DMMn, where n represents the number of repeating groups in the oligomer.

Methanol can be converted to formaldehyde via oxidation, according to Equation 2:

(2)

Figure 1A:
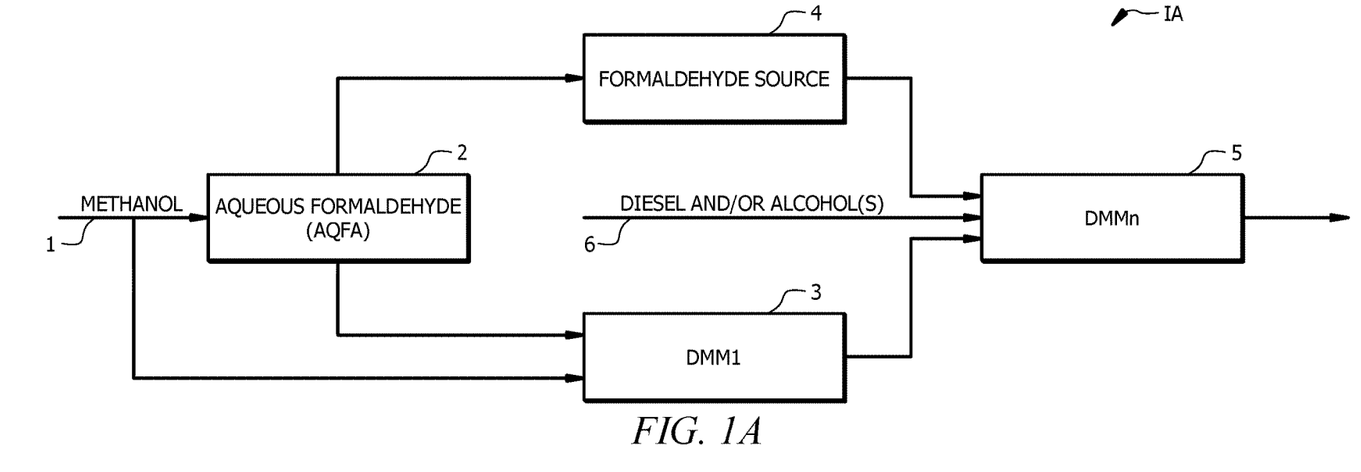
FIG. 1A is a schematic of a method IA for producing dimethoxymethane oligomers (DMMn), according to an embodiment of this disclosure.

As depicted in the embodiment of FIG. 1A, methanol 1 and aqueous formaldehyde 2 (which may be produced therefrom via Eq. (2)) can be employed to produce dimethoxymethane or DMM monomer (DMM1) 3 according to Equation 3:

(3)

In the presence of an acidic catalyst and a formaldehyde source 4, DMM monomer 3 can be oligomerized to produce a reaction effluent comprising dimethoxymethane oligomers, DMMn, 5. According to this disclosure and described in detail hereinbelow, separation of the DMMn from the reaction effluent is performed in the presence of a distillate fuel and/or one or more alcohols 6. In embodiments, the formaldehyde source 4 is an anhydrous formaldehyde source, such as trioxane or paraformaldehyde. In embodiments, the formaldehyde source 4 comprises anhydrous formaldehyde. As utilized herein, the term 'anhydrous' when utilized with certain components, such as anhydrous formaldehyde, indicates a small water content. For example, anhydrous formaldehyde may comprise less than or equal to 0.1, 1.0, or 2.0 wt % water, essentially no water, or a combination thereof.

Figure 1B:
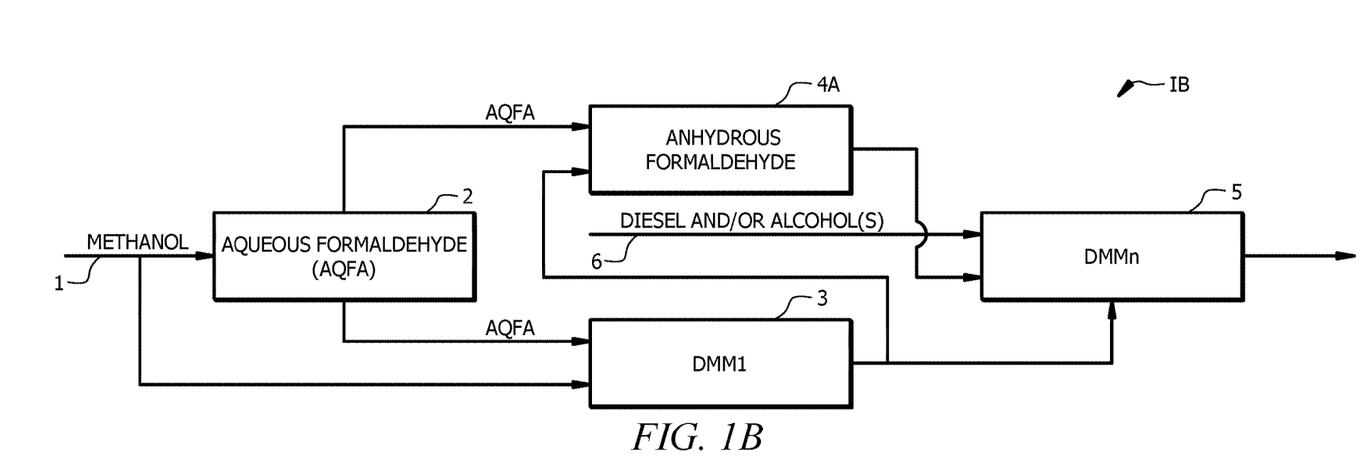
FIG. 1B is a schematic of a method IB for producing dimethoxymethane oligomers (DMMn), according to an embodiment of this disclosure.

In embodiments, as depicted in the embodiment of FIG. 1B, aqueous formaldehyde 2 can be utilized to produce anhydrous formaldehyde utilized as formaldehyde source 4A. An aqueous aldehyde, such as aqueous formaldehyde, can be reacted with an alcohol to produce a hemiacetal, such as hemiformal. Separation of water from the hemiacetal and decomposition thereof can be utilized to produce an anhydrous aldehyde, such as anhydrous formaldehyde. According to embodiments of this disclosure and described in detail hereinbelow, production of the anhydrous formaldehyde 4A can include distillation of an anhydrous formaldehyde stream 4A in the presence of DMM monomer 3 for the separation of unreacted alcohol therefrom to provide an anhydrous formaldehyde source containing anhydrous formaldehyde and DMM1. As indicated in FIG. 1B, in the presence of an acidic catalyst and the anhydrous formaldehyde source 4A containing anhydrous formaldehyde and DMM1, the DMM1 therein and additional DMM1 3 can be oligomerized to produce a reaction effluent comprising dimethoxymethane oligomers, DMMn, 5. As noted above, separation of the DMMn from the reaction effluent can be performed in the presence of a distillate fuel and/or one or more alcohols 6.

DMM Oligomerization System and Method

A DMMn oligomerization system and method according to this disclosure will now be described with reference to FIG. 2, which is a schematic of a DMMn production system 100, according to an embodiment of this disclosure. DMMn production system 100 comprises a DMMn reactor 110, a first distillation column 120, and parallel second distillation columns 130A and 130B.

The DMMn reactor is configured for reacting a formaldehyde source and DMM1 in the presence of an acidic catalyst to produce a reactor effluent comprising DMMn. DMM1 is introduced into DMMn reactor 110 via DMM1 inlet line 101. A formaldehyde source is introduced into DMMn reactor 110 via formaldehyde source inlet line 102. The formaldehyde source may or may not contain DMM1. Cooler C1 may be utilized to adjust the temperature of the formaldehyde source in formaldehyde source inlet line 102. A pump P1 may be utilized to pump DMM1 in DMM1 inlet line 101 and formaldehyde source in formaldehyde source inlet line 102 into DMMn reactor 110. A mixer M1 may be utilized to combine the DMM1 in DMM1 inlet line 101 with the formaldehyde source in formaldehyde source inlet line 102 to provide a combined stream in line 103. The combined stream in line 103 may be combined with DMM1-2 extracted as an overhead from first distillation column 120 via first distillation column overhead line 125 and recycled to DMMn reactor 110 via a pump P2, and with light components extracted from flash vessels 115A and/or 115B via flash overhead recycle line 119. A mixer M2 may produce a DMMn reactor feed via mixing of the combined stream in line 103 with the DMM1-2 in first distillation column overhead line 125, and the light components in flash overhead recycle line 119. The reactor feed may be introduced into DMMn reactor 110 via DMMn reactor feed line 104 and feed heater H1.

DMMn production reactor 110 is configured for reacting the formaldehyde source and dimethoxymethane monomer (DMM1) in the presence of an acidic catalyst to produce a reactor effluent comprising DMMn and unreacted DMM1, which can be removed from DMMn reactor 110 via reactor effluent line 111. In embodiments, DMMn reactor 110 is operable at a temperature in the range of from 40° C. to 100° C., from 40° C. to 80° C., or from 40° C. to 60° C., a pressure in the range of from 100 kPa to 4000 kPa, from 100 kPa to 500 kPa, or from 100 kPa to 300 kPa, or a combination thereof. As the presence of 1 wt % water or alcohol (e.g., methanol) can double the DMM oligomerization time, in embodiments, reacting of the formaldehyde source and the DMM1 in DMMn reactor 110 is effected in the presence of less than or equal to 5, 1, or 0.1 wt % water, less than or equal to 5, 1, or 0.1 wt % alcohol, or less than or equal to 5, 1, or 0.1 wt % water and less than or equal to 5, 1, or 0.1 wt % alcohol. At least a portion of the DMM1 in DMM1 inlet line 101 (and/or DMM1 inlet line 153, described further hereinbelow with reference to FIG. 3) may be produced via reaction of aqueous formaldehyde with methanol as per Eq. (3).

In embodiments, the formaldehyde source, the DMM1, or both (e.g., in lines 101 and/or 102 of the embodiment of FIG. 2, and/or lines 102',152, and/or 153 discussed hereinbelow with reference to the embodiment of FIG. 3) comprises or is produced at least in part from a renewable source, such as, without limitation methanol from synthesis gas which is derived from gasification of plastic waste, municipal solid waste, bio-waste, agricultural crops, or a combination thereof. In embodiments, the formaldehyde source, the DMM1, or both are produced from a renewable source in combination with fossil fuels.

In embodiments, the formaldehyde source comprises an anhydrous source of formaldehyde. In embodiments, the formaldehyde source is selected from formaldehyde, trioxane, paraformaldehyde, or combinations thereof. In embodiments, the formaldehyde source comprises or provides formaldehyde containing a water level such that the reacting of the formaldehyde source and DMM1 is effected in the presence of less than or equal to 0.1, 1.0, or 2.0 wt % water. In embodiments, the formaldehyde source comprises or provides anhydrous formaldehyde (e.g., comprising less than or equal to 0.1, 1.0, or 2.0 wt % water, essentially no water, or a combination thereof). In embodiments, the formaldehyde source comprises anhydrous formaldehyde containing a water level such that the reacting of the formaldehyde source and DMM1 is effected in the presence of less than or equal to 0.1, 1.0, or 2.0 wt % water. In embodiments, the formaldehyde source comprises anhydrous formaldehyde and DMM1, which may be produced as described with reference to FIG. 3, hereinbelow.

The acidic catalyst in DMMn reactor 110 may comprise one or more acidic zeolites, macroreticular structures with H+ functionality, or the like. For example, in embodiments, the acidic catalyst in DMMn reactor 110 comprises AMBERLYST® 15, ZSM-5, AMBERLYST® 46, or a combination thereof.

Light components may be removed from the reactor effluent in reactor effluent line 111. For example, in the embodiment of FIG. 2, the reactor effluent in reactor effluent line 111 is introduced into a first flash vessel 115A, whereby an overhead comprising light components removed via first flash vessel light overhead line 117A is separated from heavy components removed via first flash vessel heavy outlet line 116A. The heavy components removed via first flash vessel heavy outlet line 116A may be introduced into a second flash vessel 115B, and flashed components removed via a second flash vessel light overhead line 117B and heavy components removed from second flash vessel 115B via second flash vessel heavy outlet line 116B. The flashed components in first flash vessel light overhead line 117A and second flash vessel light overhead line 117B may be combined, for example via a mixer M3, to provide a combined flash overhead which may be introduced, via a cooler C2, a pump P3, flash overhead recycle line 119, mixer M2, heater H1, DMMn reactor feed line 104, or a combination thereof, into DMMn reactor 110.

The light components removed via flashing in first flash vessel 115A, second flash vessel 115B, or both may comprise water, unreacted formaldehyde source, DMM1, DMM2, or a combination thereof.

The DMMn reactor effluent, from which light components have been removed (e.g., flashed), in second flash vessel heavy outlet line 116B comprises DMMn and unreacted DMM1. According to this disclosure, DMM1-2 including unreacted DMM1 and DMMn having a chain length n equal to 2 (DMM2), dimethoxymethane oligomers having a chain length n in the range of from 2-5 (DMM2-5), dimethoxymethane oligomers having a chain length n of greater than or equal to 5 (DMM5+), or a combination thereof are separated from the DMMn reactor effluent (e.g., the DMMn reactor effluent in DMMn reactor effluent line 111 or second flash vessel heavy outlet line 116B). According to this disclosure, the separating comprises distillation in the presence of at least one alcohol, a distillate fuel, or both, as described hereinbelow. In the embodiment of FIG. 1, a line 121A is configured to introduce a first alcohol into first distillation column 120, a line 121B is configured to introduce a second alcohol into first distillation column 120, and a first distillate or diesel line 122A is configured to introduce distillate into first distillation column 120. In embodiments, no distillate fuel is introduced into first distillation column 120.

A mixer M4 may be operable to combine the reactor effluent in second flash vessel heavy outlet line 116B, the first alcohol in line 121A, the second alcohol in line 121B, and the distillate in first distillate inlet line 122A to provide a first distillation column feed line, which is introduced into first distillation column 120 via first distillation column feed line 123. The first distillation column feed line 123 may introduce the first distillation column feed comprising DMMn reactor effluent into first distillation column 120 at a mid-point of first distillation column 120.

In embodiments, first distillation column 120 is configured for operation with a first distillation column feed comprising from 45 to 100, from 45 to 90, from 45 to 50, from 90 to 100, from 80 to 100, or from 40 to 100 weight percent (wt %) of the DMMn reactor effluent, from 0.1 to 10.0, from 0.5 to 10.0, from 0.5 to 6.0, from 0.5 to 2.0, from 0.1 to 3.0, or from 0.1 to 1.5 wt % of the at least one alcohol, from 0 to 60, from 0 to 50, from 0 to 20, from 0 to 30, or from 10 to 50 wt % of the distillate fuel, or a combination thereof.

First distillation column 120 is configured to separate, from the reactor effluent, a first distillation column overhead comprising DMM1-2, including unreacted DMM1 and DMMn having a chain length n equal to 2 (DMM2), from a first distillation column bottoms comprising DMMn wherein n is greater than or equal to 2 (DMM2+). The first distillation column overhead is removed from first distillation column 120 via first distillation column overhead line 125. As noted hereinabove, at least a portion of the first distillation column overhead 125 is recycled to DMMn reactor 110, whereby additional DMMn may be produced from the DMM1 and/or DMM2 therein. The first distillation column bottoms comprising DMM2+ is extracted from first distillation column 120 via first distillation column bottoms line 124. First distillation column 120 may be configured and/or operated to provide a desired amount of DMM2 in the first distillation column bottoms comprising DMM2+. For example, in embodiments, the amount of DMM2 allowed in the first distillation column bottoms is an amount that will result in less than a desired percentage (e.g., less than 1 wt %) of DMM2 in a final product after blending with distillate to a desired DMMn percentage, which may be, for example, 5 wt %, 10 wt %, or 15 wt % (e.g., the final DMM product extracted via DMMn product line 148, or after additional blending of distillate therewith).

As noted above, in embodiments, the DMMn distillation is effected in the presence of at least one alcohol, which reacts with free formaldehyde, thus decreasing the concentration thereof in the system. Although indicated as being introduced into first distillation column 120, in embodiments, the alcohol may be introduced elsewhere in DMMn production system 100, for example, downstream of first distillation column 120, into second distillation column 130A/130B, upstream of second distillation column 130A/130B, or a combination thereof. Thus, in embodiments, the DMMn production system according to this disclosure comprises an inlet line configured for the introduction of the at least one alcohol into the first distillation column, an inlet line configured for the introduction of the at least one alcohol into the second distillation column, or both.

In embodiments, the at least one alcohol (e.g., the first alcohol introduced via first alcohol inlet line 121A, the second alcohol introduced via second alcohol inlet line 121B, or both) comprises a low volatility alcohol, as evidenced by a boiling point of greater than or equal to 100° C., 150° C., 160° C., 170° C., 180° C., 190° C., 200° C. or 210°, a boiling point in the range of from 95° C. to 220° C., from 95° C. to 170° C., from 110° C. to 220° C., from 110° C. to 170° C., from 95° C. to 110° C., from 110° C. to 170° C., or from 170° C. to 220° C., or a combination thereof. In embodiments, the at least one alcohol has a low water solubility, as indicated by a water solubility of less than or equal to 25 g/100 mL, 20 g/100 mL, 15 g/100 mL, 10 g/100 mL, 9 g/100 mL, 8 g/100 mL, 7 g/100 mL, 6 g/100 mL, 5 g/100 mL, or 4 g/100 mL at 20° C., less than or equal to 1 g/100 mL, 5 g/100 mL, or 10 g/100 mL at 30° C., or a combination thereof. In embodiments, the at least one alcohol is selected from methanol, ethanol, propanol, isobutanol, cyclohexanol, octanol, benzyl alcohol, phenylethanol, hexadecanol, or a combination thereof.

In embodiments, the at least one alcohol comprises an alcohol produced from a renewable feedstock, such as, without limitation, bio-butanol and/or higher carbon number bio-alcohol(s). As used herein, the terms bio-alcohol and bio-butanol refer to an alcohol and butanol, respectively, produced from a renewable source, such as biomass. In embodiments, the at least one alcohol comprises a blend of at least two (three, or more) alcohols, at least two (three or more) alcohols introduced at at least two (three or more) different places relative to the distillation, or both. The at least two (or three or more) alcohols may be introduced together (e.g., as a blend), or separately, for example, via first alcohol inlet line 121A and second alcohol inlet line 121B, respectively. In embodiments, the blend comprises a first alcohol and a second alcohol having a different volatility from that of the first alcohol. In embodiments, the blend further comprises a third alcohol having a different volatility than that of the first alcohol, the second alcohol or both. The blend of alcohols may include a first alcohol introduced via first alcohol inlet line 121A and a second alcohol introduced via second alcohol inlet line 121B. In embodiments, the second alcohol may have a boiling point greater than that of the first alcohol such that the first distillation bottoms comprises at least a portion of the second alcohol. For example, in embodiments, the first alcohol introduced via first alcohol inlet line 121A comprises methanol, ethanol, propanol, isobutanol, cyclohexanol, octanol, benzyl alcohol, phenylethanol, hexadecanol, or a combination thereof, and the second alcohol introduced via second alcohol inlet line 121B comprises a different alcohol selected from methanol, ethanol, propanol, isobutanol, cyclohexanol, octanol, benzyl alcohol, phenylethanol, hexadecanol, or a combination thereof.

In embodiments, deposited paraformaldehyde and associated solids are removed by heating (e.g., to a temperature of greater than 180° C., 200° C., or 220° C.), and reaction of any free formaldehyde generated with the at least one alcohol to reduce a free formaldehyde content. Reduction in the free formaldehyde content reduces formaldehyde emissions and/or potential personnel exposure to free formaldehyde during a cleaning operation.

As noted above, the production of DMMn according to this disclosure may utilize distillate as a diluent to reduce viscosity and inhibit deposition of heavier oligomers throughout the DMMn distillation system. Although indicated as being introduced into first distillation column 120, in embodiments, the distillate may be introduced elsewhere in DMMn production system 100, for example, downstream of first distillation column 120, into second distillation column 130A/130B, upstream of second distillation column 130A/130B, downstream of second distillation column 130A/130B, or a combination thereof. The distillate may comprise diesel fuel. In embodiments, the diesel comprises renewable diesel, such as, without limitation, biodiesel. Biodiesel refers to diesel fuel produced from a non-fossil fuel source, such as vegetable oil or animal fat.

Thus, in embodiments, a DMMn production system according to this disclosure comprises an inlet line configured for the introduction of the distillate fuel into the first distillation column, an inlet line configured for the introduction of the distillate fuel into the second distillation column, or a combination thereof.

First alcohol inlet line 121A may be configured for the introduction of the first alcohol (with or separately from the DMMn process stream, the second alcohol, and/or the distillate) into a top portion of the first distillation column, the second distillation column, or both; second alcohol inlet line 121B may be configured for the introduction of the second alcohol (with or separately from the DMMn process stream, the first alcohol, and/or the distillate) into a top portion of the first distillation column, the second distillation column, or both; first distillate inlet line 122A may be configured for the introduction of distillate (with or separately from the DMMn process stream, the first alcohol, and/or the second alcohol) into a top portion of the first distillation column, the second distillation column, or both; and/or second distillate inlet line 122B (described hereinbelow) may be configured for the introduction of distillate (with or separately from the DMMn process stream, the first alcohol, and/or the second alcohol) into a top portion of the first distillation column, the second distillation column, or both, and/or a second distillate inlet line 122B may be configured for the combination of distillate with the purified DMM2-5 stream in purified DMM2-5 line 142, for example via mixer M7. Alternatively or additionally, the first alcohol, the second alcohol, and/or the distillate may be introduced elsewhere in system 100. In embodiments, the alcohol(s) is (are) introduced above the feed tray, such that a minimum level (e.g., 1% to 2%) is maintained at every location in the distillation column profile. The introduction point can depend on the alcohol(s) utilized, the operating conditions (e.g., temperature and/or pressure), which can vary with a desired level of DMM2 in the first distillation column bottoms, a diluent level, a percent recycle to the second distillation column, or a combination thereof.

The first distillation column bottoms comprising DMM2+ is introduced into a second distillation column configured to separate, from the first distillation column bottoms, a second distillation column overhead comprising dimethoxymethane oligomers having a chain length n in the range of from 2-5 (DMM2-5) from a second distillation column bottoms comprising dimethoxymethane oligomers having a chain length n of greater than or equal to 5 (DMM5+). In the embodiment of FIG. 2, the first distillation column bottoms comprising DMM2+ in first distillation column bottoms line 124 is split via splitter S1 and lines 124A and 124B to provide portions of the first distillation column bottoms comprising DMM2+ into each of two second distillation columns 130A, and 130B, respectively.

In embodiments, the first distillation column bottoms is introduced into the second distillation column at a point in an upper section or upper half of second distillation columns 130A/130B. For example, the first distillation column bottoms in first distillation column bottoms lines 124A and 124B may be introduced into second distillation columns 130A and 130B, respectively, at a point above the midpoint of second distillation columns 130A/130B.

Second distillation columns 130A and 130B are configured and/or operated to provide a second distillation column overhead comprising DMM2-5, removed therefrom via second distillation column overhead lines 127A and 127B, respectively, and a second distillation column bottoms comprising DMM5+, removed therefrom via second distillation column bottoms lines 126A and 126B, respectively. Second distillation column 130A/130B may be configured and/or operated to provide a desired amount of DMM5 in the second distillation column overhead comprising DMM2-5. For example, in embodiments, the amount of DMM5 allowed in the second distillation column overhead is an amount that will result in less than a desired percentage (e.g., less than 1 wt %) of DMM5 in a final product after blending with distillate to a desired DMMn percentage, which may be, for example, 5 wt %, 10 wt %, or 15 wt % (e.g., the final DMM product extracted via DMMn product line 148, or after additional blending of distillate therewith). For example, the second distillation column overhead may comprise less than or equal to 2 wt % DMM5, while the second distillation column bottoms may comprise the balance of the DMM5.

At least a portion of the second distillation bottoms may be recycled to the second distillation column, for example via second distillation column bottoms recycle lines 126A" and 126W, respectively. The at least a portion of the second distillation bottoms recycled to the second distillation column may be combined with the first distillation column bottoms to provide a second distillation column feed, in embodiments. For example, a portion of the second distillation column bottoms in second distillation column bottoms recycle line 126A" may be combined with the first distillation column bottoms in line 124A prior to introduction into second distillation column 130A, and a portion of the second distillation column bottoms in second distillation column bottoms recycle line 126B" may be combined with the first distillation column bottoms in line 124B prior to introduction into second distillation column 130B. In embodiments, the first distillation column bottoms and the portion of the second distillation column bottoms are introduced separately into second distillation column 130A/130B. For example, in embodiments, the portion of the second distillation column bottoms in second distillation column bottoms recycle line 126A" and the portion of the second distillation column bottoms in second distillation column bottoms recycle line 126B" are introduced into second distillation column 130A and 130B, respectively, at a point within a lower section or lower half of the respective second distillation column. The recycle may provide for an increased level of distillate fuel diluent in second distillation column 130A/130B, thus requiring less fresh diluent to achieve a desired level of dilution in the column.

In embodiments, the second distillation column is configured for operation with a second distillation column feed comprising from 80 to 100, from 90 to 100, or from 95 to 100 weight percent (wt %) of the first distillation column bottoms, from 0 to 20, from 0 to 10, or from 0 to 5 wt % of the recycled second distillation column bottoms, or a combination thereof.

As noted above, distillate can be introduced downstream of second distillation column 130A/130B, in embodiments. For example, as indicated via dotted line in FIG. 2, in embodiments distillate fuel in second distillate inlet line 122B is combined, for example via mixer M5, with the second distillation column overhead in second distillation column overhead lines 127A and 127B, to provide a combined DMM2-5 stream in second distillation column combined overhead line 128. Distillate fuel may be combined with the second distillation column overhead to provide blending to a desired wt % DMMn in the final product. For example, as indicated via solid line in FIG. 2, line 122B may be configured to combine distillate fuel with purified DMM2-5 stream in purified DMM2-5 line 142, for example via mixer M7. In such embodiments, a line 122B may or may not also combine the distillate fuel, for example via mixer M5, with the second distillation column overhead in second distillation column overhead lines 127A and 127B. In other embodiments, the blending of distillate, as indicated by mixer M7, is performed at a blending terminal or somewhere outside DMMn production system 100.

Acid, base, water, formaldehyde, or a combination thereof may be removed from the second distillation column overhead via a removal apparatus to provide a purified DMM2-5 stream. The removal apparatus may comprise a cooler, a filter, an adsorbent, or a combination thereof, and removing acid, base, water, formaldehyde, or a combination thereof from the second distillation column overhead can be effected via cooling (to a temperature in the range of from 50° C. to 100° C., from 35° C. to 50° C., or from 20° C. to 35° C.), filtration, contact with an adsorbent, or a combination thereof. Without limitation, the adsorbent can comprise calcium carbonate, hydroxide, alumina, activated carbon, adsorbent clay, or another adsorbent effective for adsorbing acid, base, water, aldehyde, or a combination thereof. For example, in the embodiment of FIG. 2, cooler C3 may be utilized to reduce the temperature of the combined stream in second distillation column combined overhead line 128 comprising DMM2-5, and apparatus 140 may be operated to remove one or more component from the DMM2-5. Removed components (e.g., aqueous formaldehyde) may be extracted from removal apparatus 140 via removed component(s) line 141. A purified DMM2-5 stream may be extracted from removal apparatus 140 via purified DMM2-5 line 142. In embodiments, acid removal from DMMn can be effected by treating the stream with a base such as $CaCO_3$, $MgOH_2$, amines, NaOH, or the like. In this manner, the acid present in the stream comprising DMMn that is being treated can be removed or neutralized. Without such removal of the acid, DMMn oligomers can continue to react and generate larger DMMn oligomers, thus causing undesirable properties, such as, without limitation, solid formation or a change in oligomer distribution.

Figure 2:
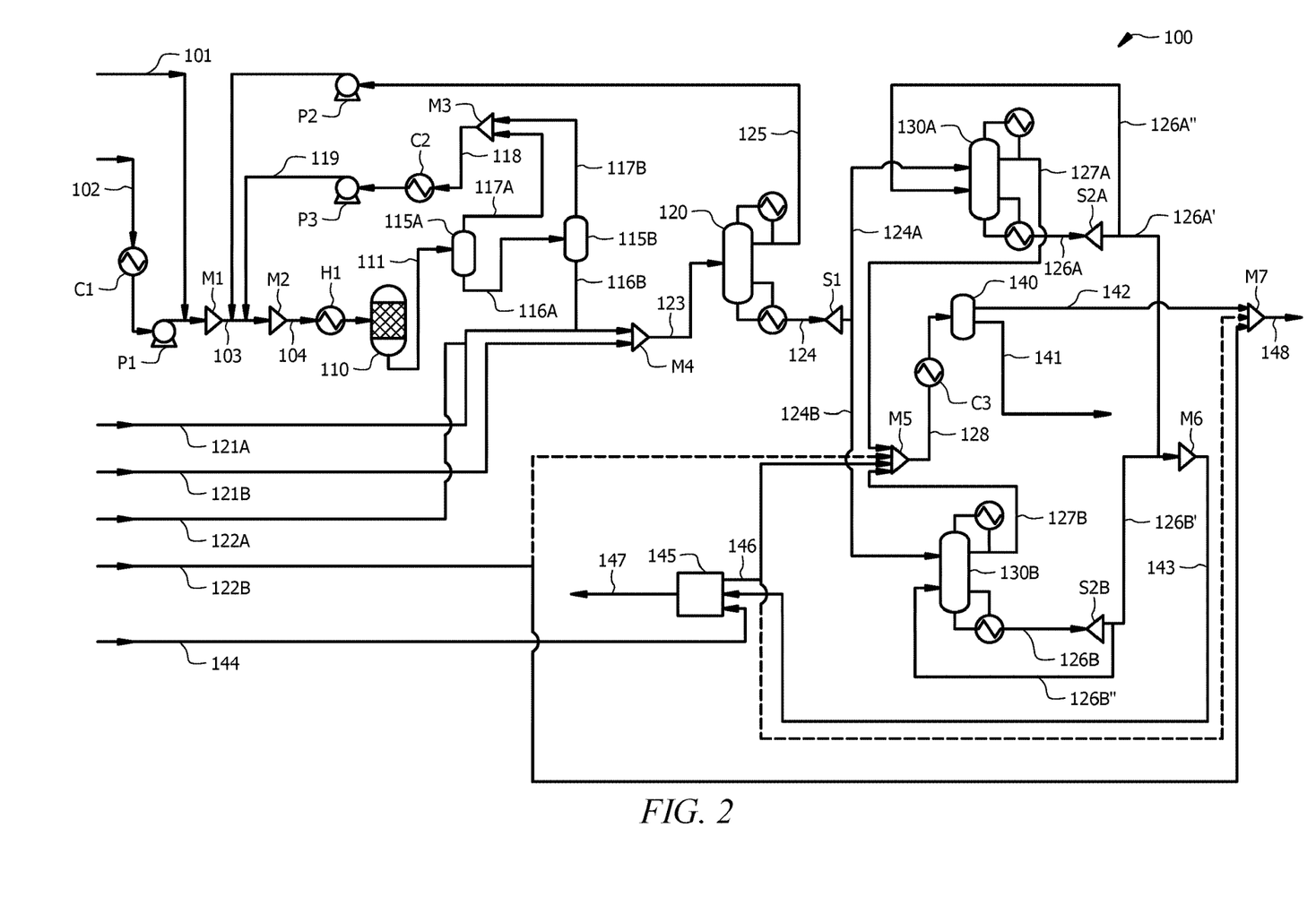
FIG. 2 is a schematic of a dimethoxymethane oligomer (DMMn) production system 100, according to an embodiment of this disclosure.

Although indicated as downstream of second distillation columns 130A and 130B in the embodiment of FIG. 2, removing trace acid, base, or both may be effected elsewhere in DMMn production system 100. For example, a removal step can comprise removing acid, base, or both from a reaction stream comprising the reaction effluent comprising DMMn (i) downstream of a DMMn production reactor in which the reaction effluent comprising DMMn is produced (e.g., from reaction effluent in DMMn reactor effluent line 111, second flash vessel heavy outlet line 116B and/or first distillation column feed line 123), (ii) upstream of the separating (e.g., from reaction effluent in DMMn reactor effluent line 111, second flash vessel heavy outlet line 116B and/or first distillation column feed line 123), (iii) between separating of DMM1-2 and separating of DMM2-5 from the reaction effluent (e.g., from reaction effluent in first distillation column bottoms lines 124, 124A, and/or 124B), (iv) subsequent separating of DMM2-5 from the reaction effluent comprising DMMn (e.g., from reaction effluent in second distillation column overhead lines 127A, 127B, and/or 128), or (v) a combination thereof. Thus, a removal apparatus 140 can be located downstream of DMMn reactor 110, upstream of first distillation column 120, downstream of second distillation column 130A/130B, between DMMn reactor 110 and first distillation column 120, between first distillation column 120 and second distillation column 130A/130B, or a combination thereof Without wishing to be limited by theory, acid leaching from the acidic catalyst can cause delayed solid formation in the DMM2-5 product, and thus acid removal may be desired.

In embodiments, distillate fuel is recovered from at least a portion of the second distillation column bottoms. The distillate fuel may be recovered from the at least a portion of the second distillation column bottoms via extraction with an extractant, chilling, centrifugation, other filtration, or a combination thereof to produce a heavy oligomer product comprising DMM5+ and a recovered stream comprising the distillate fuel, DMMn, or a combination thereof. In embodiments, the recovered stream comprises less than or equal to 10, 9, 8, 7, 6, 5, 4, 3, 2, 1, or 0 wt % DMMn, or from 1 to 10, from 1 to 5 or from 1 to 2 wt % DMMn, wherein n is primarily 5 or greater.

For example, DMMn production system 100 of the embodiment of FIG. 2 comprises extractor 145 configured to separate from the second distillation column bottoms in second distillation column bottoms lines 126A' and 126B' (which may be combined via a mixer M6 to provide a combined second distillation column purge line 143), via extraction with an extractant introduced via extractant inlet line 144, a recovered stream comprising the distillate fuel, which may be removed from extractor 145 via recovered distillate line 146. A heavy oligomer stream comprising DMM5+ may be removed from extractor 145 via heavy oligomer outlet line 147. As indicated via dotted line in FIG. 2, the recovered distillate stream in recovered distillate line 146 (after extraction of DMM5+ in vessel/extractor 145) may be combined, for example via a mixer M7, with the purified DMM2-5 stream in purified DMM2-5 line 142 and/or with the DMM2-5 in second distillation column combined overhead line 128 to provide a DMMn product, which may be removed from DMMn production system 100 via DMMn product line 148. Alternatively or additionally, as indicated via solid line in FIG. 2, the recovered distillate stream in recovered distillate line 146 may be combined with the DMM2-5 product in second distillation column overhead lines 127A and/or 127B, for example via mixer M5, and thus introduced into a removal apparatus 140 configured to remove acid, base, water, formaldehyde, or a combination thereof therefrom.

It is noted that the DMM5+ in the heavy oligomer stream comprising DMM5+ that is removed from extractor 145 via heavy oligomer outlet line 147 may also be utilized as a non-distillate fuel, in embodiments.

The extractant introduced into extractor 145 via extractant inlet 144 can comprise an alcohol, water, or both. In embodiments, the extractant comprises an alcohol selected from methanol, ethanol, propanol, isobutanol, cyclohexanol, octanol, benzyl alcohol, phenylethanol, hexadecanol, or a combination thereof. In embodiments, methanol is utilized for the efficient removal of DMM5+ oligomers from distillate/diesel. In embodiments, the extractant comprises at least one alcohol utilized in the separating, from the reaction effluent, of DMM1-2, DMM2-5, DMM5+, or a combination thereof, as described above. For example, the extractant may comprise one or more of the alcohols described hereinabove with reference to the first alcohol introduced via first alcohol inlet line 121A and the second alcohol introduced via second alcohol inlet line 121B. In embodiments, the extractant comprises at least one of the at least one alcohols in the presence of which first distillation column 120, second distillation column 130A/130B, or a combination thereof are operated.

In embodiments, water, alcohol, or both are removed from the heavy oligomer product comprising DMM5+ in heavy oligomer outlet line 147, and at least a portion of the heavy oligomer product from which the water, alcohol, or both has been removed is recycled. Thus, DMMn production system 100 can further comprise separation apparatus (not shown in the embodiment of FIG. 2) configured to remove water, alcohol, or both from the heavy oligomer stream comprising DMM5+ in heavy oligomer outlet line 147, and a heavy oligomer recycle line configured to recycle at least a portion of the heavy oligomer stream from which the water, alcohol, or both has been removed to a level suitable for recycling. The heavy oligomer stream in heavy oligomer outlet line 147 from which the water, the alcohol, or both has been removed can, in embodiments, be recycled to DMMn reactor 110, first distillation column 120, second distillation column 130A/130B, or a combination thereof. Water, alcohol, or both may be removed from the heavy oligomer product such that the heavy oligomer product from which the water, the alcohol, or both has been removed, and a portion of which may be recycled, can comprise levels of water, alcohol, or both, such that the reacting of the formaldehyde source and the DMM1 is performed in the presence of less than or equal to 5, 1, or 0.1 wt % water, less than or equal to 5, 1, or 0.1 wt % alcohol, or less than or equal to 5, 1, or 0.1 wt % water and less than or equal to 5, 1, or 0.1 wt % alcohol, in embodiments. In embodiments, the heavy oligomer product may be depolymerized, for example in the presence of acidic species, prior to recycling.

Anhydrous Formaldehyde Production Method

As noted hereinabove, the formaldehyde source may comprise any anhydrous formaldehyde source, such as, without limitation, anhydrous formaldehyde, trioxane, paraformaldehyde, or combinations thereof. In embodiments, the formaldehyde source comprises or provides formaldehyde containing a water level such that the reacting of the formaldehyde source and DMM1 is effected in the presence of less than or equal to 0.1, 1.0, or 2.0 wt % water. In embodiments, the formaldehyde source comprises or provides anhydrous formaldehyde (e.g., comprising less than or equal to 0.1, 1.0, or 2.0 wt % water, essentially no water, or a combination thereof). In embodiments, the formaldehyde source comprises anhydrous formaldehyde containing a water level such that the reacting of the formaldehyde source and DMM1 is effected in the presence of less than or equal to 0.1, 1.0, or 2.0 wt % water.

Although 1,3,5-trioxane has been reported in the literature as a suitable monomer for production of DMMn, the production of 1,3,5-trioxane via the sulfuric acid method has many shortcomings. According to embodiments of this disclosure, anhydrous formaldehyde can be utilized as the formaldehyde source for DMMn production. Description of a system and method of producing a formaldehyde source comprising anhydrous formaldehyde and DMM1 will now be made with reference to FIG. 3, which is a schematic of an anhydrous formaldehyde production system 150, according to an embodiment of this disclosure. Anhydrous formaldehyde production system 150 comprises hemiacetal production reactor 160, decanter 170, separator 180, decomposition vessel 190, and distillation column 195.

Figure 3:
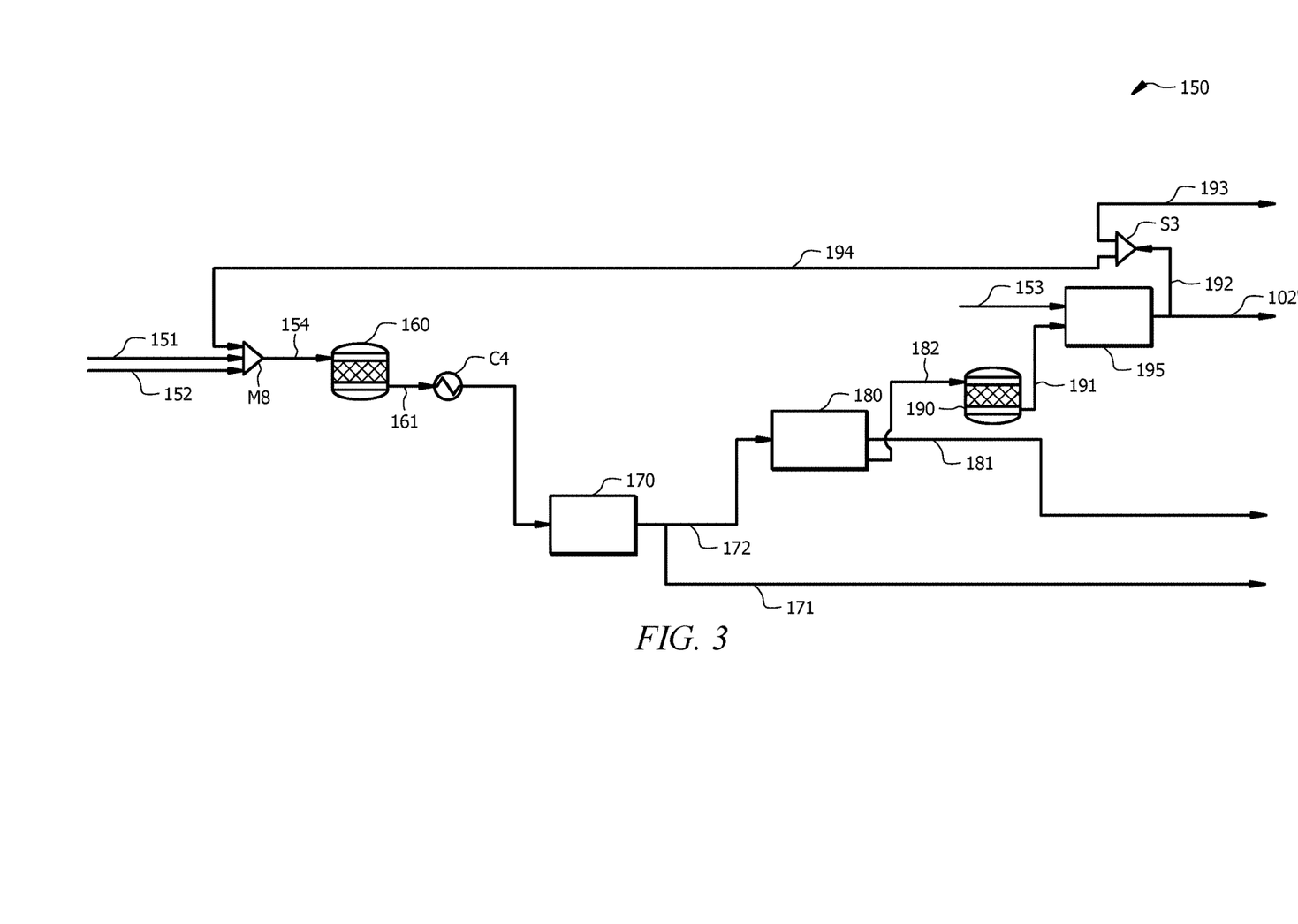
FIG. 3 is a schematic of an anhydrous formaldehyde production system 150, according to an embodiment of this disclosure.

Aqueous formaldehyde is introduced into hemiacetal production reactor 160 via aqueous formaldehyde inlet line 152. The aqueous formaldehyde can comprise from 40 to 90, from 50 to 90, or from 60 to 90, or greater than or equal to 50, 60, or 70 wt % formaldehyde. An alcohol is introduced into hemiacetal production reactor 160 via fresh alcohol inlet line 151 and/or recycle alcohol line 194. The alcohol reacted with the aqueous formaldehyde can comprise a low solubility alcohol, as indicated by a water solubility of less than or equal to 25 g/100 mL, 20 g/100 mL, 15 g/100 mL, 10 g/100 mL, 9 g/100 mL, 8 g/100 mL, 7 g/100 mL, 6 g/100 mL, 5 g/100 mL, or 4 g/100 mL at 20° C., less than or equal to 1 g/100 mL, 5 g/100 mL, or 10 g/100 mL at 30° C., or a combination thereof. In embodiments, the alcohol reacted with the aqueous formaldehyde is selected from cyclohexanol, isobutanol, phenylethanol, or a combination thereof. A mixer M8 may combine the aqueous formaldehyde in line 152 with the alcohol in fresh alcohol inlet line 151 and/or recycle alcohol line 194 to provide a hemiacetal feed, which may be introduced into hemiacetal production reactor 160 via hemiacetal feed inlet line 154.

Hemiacetal production reactor 160 is operable to carry out the reaction of the aqueous formaldehyde with the alcohol to produce a hemiacetal reactor effluent comprising aqueous hemiformal, which may be removed from hemiacetal production reactor 160 via hemiacetal reactor effluent outlet line 161. Hemiacetal production reactor 160 may be any reactor known in the art for the production of hemiacetal from aldehyde. The hemiacetal reactor effluent may be cooled via a cooler C4 (to a temperature in the range of from 10° C. to 50° C., from 10° C. to 30° C., or from 10° C. to 20° C., or less than or equal to 50° C., 30° C., or 20° C. ° C.).

An anhydrous formaldehyde production system according to this disclosure can comprise water removal apparatus configured to remove water from the hemiacetal reactor effluent comprising aqueous hemiformal. The water removal apparatus can comprise one or more units selected from decanters, filtration units, adsorbers, absorbers, or a combination thereof. In the embodiment of FIG. 3, the water removal apparatus comprises: a decanter 170 configured to separate an aqueous phase comprising water from an organic phase comprising the hemiformal; and a separator 180 configured to separate water from the organic phase via membrane filtration, another separation, or a combination thereof, to provide an anhydrous hemiformal. Thus, the cooled, aqueous hemiformal in hemiacetal reactor effluent line 161 is introduced into decanter 170, wherein an organic phase comprising the hemiformal is decanted from an aqueous phase comprising water. The organic phase is removed from decanter 170 via organic phase outlet line 172, and the aqueous phase is removed from decanter 170 via aqueous phase outlet line 171. The organic phase can comprise from 70 to 90, from 70 to 85, from 70 to 80, or less than or equal to 90, 80, or 70 wt % water, with the balance hemiacetal. For example, the organic phase can comprise from 10 to 30, from 15 to 30, from 20 to 30, or greater than or equal to 10, 20, or 30 wt % hemiformal, in embodiments.

The organic phase is introduced into separator 180 via organic phase outlet line 172. Separator 180 is operable to separate water, which is removed therefrom via water outlet line 181, from a reduced-water hemiformal stream, which is removed from separator 180 via anhydrous hemiformal outlet line 182. Separator 180 can comprise one or more filtration units, adsorbers, absorbers, or a combination thereof. In embodiments, separator 180 comprises a membrane filtration apparatus.

Anhydrous formaldehyde production system 150 further comprises decomposition vessel 190 configured to decompose the hemiformal to produce formaldehyde. In embodiments, decomposition vessel 190 can comprise any suitable vessel, for example, in embodiments, decomposition vessel 190 comprises a heat exchanger. Decomposition vessel may be operated as known in the art to produce aldehyde from hemiacetal. In embodiments, decomposition vessel 190 is operable to heat the anhydrous hemiformal to a temperature of greater than or equal to 125° C., 150° C., or 175° C., whereby anhydrous formaldehyde is produced therefrom. A decomposition product comprising the anhydrous formaldehyde and unreacted alcohol is removed from decomposition vessel 190 via decomposition vessel outlet line 191.

Anhydrous formaldehyde production system 150 further comprises distillation column 195 configured to subject the decomposition product to distillation to separate a heavy stream comprising unreacted alcohol from the anhydrous formaldehyde. According to embodiments of this disclosure, the distillation of the decomposition product is performed in the presence of DMM1. Thus, DMM1 can be introduced (separately or in combination with the decomposition product in line 191) into distillation column 195 via a DMM1 inlet line 153. The DMM1 can be introduced (separately or in combination with the decomposition product in line 191) into a top portion or at a mid-point of distillation column 195 via DMM1 inlet line 153. A recycle line 194 may be configured to recycle at least a portion of the heavy stream comprising unreacted alcohol to hemiacetal production reactor 160. Excess alcohol may be removed from anhydrous formaldehyde production system 150 via excess alcohol outlet line 193.

An anhydrous formaldehyde source containing anhydrous formaldehyde and DMM1 is removed from distillation column 195 via distillation column outlet line 102'. The anhydrous formaldehyde source in line 102' may be utilized as the formaldehyde source for the production of DMMn in a DMMn production reactor (e.g., may be utilized as the formaldehyde source introduced into DMMn production reactor 110 of DMMn production system 100 of the embodiment of FIG. 2 via formaldehyde source inlet line 102).

In embodiments, the anhydrous formaldehyde source in line 102' (or 102) comprises at least 40, 70, or 100 wt % anhydrous formaldehyde, at least 0, 30, or 60 wt % DMM1, less than or equal to 0.1, 1.0, or 2.0 wt % water, or a combination thereof. Without wishing to be limited by theory, the presence of DMM1 in the anhydrous formaldehyde source may improve the mixing of the anhydrous formaldehyde and the DMM1 prior to the reacting of the formaldehyde source and the DMM1 in the presence of an acidic catalyst in a DMMn production reactor to produce a reaction effluent comprising DMMn may enhance safety relative to the use of a pure or substantially pure anhydrous formaldehyde source, or both.

Fuel Comprising DMM2-5 Product

In embodiments, all or a portion of the DMM1-2 removed from first distillation column 120 via first distillation column overhead line 125, all or a portion of the DMM2-5 product in second distillation column overhead lines 127A, 127B, or second distillation column combined overhead line 128, purified DMM2-5 line 142 or DMMn product line 148, all or a portion of the DMM5+ removed via heavy oligomer outlet line 147, distillate fuel in recovered distillate line 146, or a combination thereof, is utilized in a fuel application, a chemical application, a polymer application, or a combination thereof. For example, all or a portion of the DMM1-2 may be utilized as a solvent.

In embodiments, all or a portion of the DMM1-2, the DMM2-5, and/or the distillate fuel in recovered distillate line 146 produced according to this disclosure is used as or utilized as a component of a product composition for use as a fuel. Such a fuel may have a composition as described, for example in U.S. Patent Application No. 62/576,995, filed 25 Oct. 2017, the disclosure of which is hereby incorporated herein for purposes not contrary to this disclosure. Such product compositions comprise dimethoxymethane oligomers and distillate fuels, wherein the dimethoxymethane oligomers have specific chain length(s), wherein the product composition comprises less than a maximum total amount of dimethoxymethane oligomers, and/or wherein the product composition further comprises a stabilizer comprising one or more alcohols. Distillation in first distillation column 120, second distillation column 130A/130B, or both may be operated to provide a desired DMM1-2 product, DMM2-5 product, and/or distillate fuel in recovered distillate line 146 for including in such a product composition for use as a fuel. For example, as noted hereinabove, first distillation column 120 may be operated to provide a desired amount of DMM2 in a DMMn product in DMMn product outlet line 148.

In embodiments, a composition produced with all or a portion of the DMM1-2, the DMM2-5, and/or the distillate fuel in recovered distillate line 146 of this disclosure comprises a distillate fuel (also referred to as a distillate fuel portion or distillate fuel component of the composition) and at least a portion of the DMM1-2 product, the DMM2-5 product, and/or the distillate fuel in recovered distillate line 146 as or within an oligomer portion or oligomer component of the composition. Any distillate fuel may be utilized in the composition. In embodiments, the distillate fuel comprises diesel, jet fuel, kerosene, or a combination thereof. Combination of DMMn with a distillate fuel may provide for upgrading of low value refinery streams, in embodiments.

The compositions of this disclosure may comprise a specific total amount (e.g., volume percentage) of DMMn oligomers. For example, in embodiments, a composition according to this disclosure comprises a distillate fuel, and less than a maximum desired volume percent of various DMMn. In embodiments, the composition comprises less than or less than or equal to 20, 15, 10, 9, 8, 7, 6, 5, 4, 3, 2, or 1 volume percent DMMn, wherein volume percent is defined as a ratio of the volume of the oligomer to the sum of the volumes of the distillate fuel, any additional components (e.g., stabilizer, as described below), and the oligomer.

Product compositions comprising percentages of DMMn in accordance with the aforementioned volume percentage in blends of DMMn in distillate fuels may provide enhanced fungibility, better engine hose and seal compatibility, and/or properties more similar to conventional diesel (i.e., diesel not containing any DMMn) than compositions comprising higher volume percentages of DMMn. Utilization of a lower overall volume percentage of oligomers (e.g., less than 10 vol. %) may result in lower production cost and/or an easier path to regulatory approval than that of compositions comprising higher overall volume percentages of oligomers.

In embodiments, a composition according to this disclosure comprises a specific distribution and/or amount of DMMn oligomers. Specific ranges of chain lengths (n) of the DMMn oligomers may be incorporated to provide a composition of this disclosure.

In embodiments, a composition according to this disclosure comprises an oligomer portion comprising DMM5+. Without wishing to be limited by theory, inclusion of higher levels of oligomers having n greater than 4 can increase the cetane content of the composition, while retaining other properties appropriate for blending with a distillate fuel, such as diesel. Oligomers of higher n (e.g., n greater than 5, 6, or 7) may be limited in order to maintain certain product properties, such as cloud point and pour point. Compositions comprising DMM5+ according to this disclosure, may also comprise oligomers with n less than or equal to 4, such as DMM1, DMM2, DMM3 and/or DMM4, due to, for example, lower production cost, but content of the lower chain length (n) oligomers (e.g., DMM1, DMM2, DMM3, and/or DMM4) may be reduced to minimize the potential negative impact thereof on flash point, cetane, and/or fungibility.

For example, in embodiments, a composition according to this disclosure comprises at least one DMMn wherein n is greater than 4, i.e., DMM5+. In embodiments, the composition comprises less than 2, 1, or 0.5 volume percent DMM5+. In embodiments, the oligomer portion of the composition comprises or consists essentially of DMMn selected from DMM5 along with DMM2, DMM3, and/or DMM4. Such compositions may comprise, for example, less than or equal to 5, 10 or 20 volume percent of an oligomer portion comprising DMM2 in addition to DMM3, DMM4 and/or DMM5.

In embodiments, the oligomer portion of a composition according to this disclosure comprises primarily or consists essentially of DMM3, DMM4, or a combination thereof. In embodiments, the oligomer portion of a composition according to this disclosure comprises a desired ratio of DMM3 to DMM4 and/or DMM5. Without wishing to be limited by theory, higher amounts of DMM3 may enhance cloud point for use of the composition in colder climates, while DMM4 and/or DMM5 may be utilized to increase the cetane content.

In embodiments, the oligomer portion of the composition comprises or consists essentially or primarily of DMM2-5 (i.e., oligomers having chain lengths n of equal to or greater than 2 and less than 6), DMM2-4 (i.e., oligomers having chain lengths n of 2 and/or 3 and/or 4), DMM3 (i.e., oligomers having chain lengths n of 3), DMM4 (i.e., oligomers having chain lengths n of 4), or a combination thereof. In embodiments, the composition comprises from 0 to 0.1, from 0 to 0.5, or from 0 to 1.0 volume percent DMM2; from 0 to 1.0, from 0 to 5.0, or from 0 to 25.0 volume percent DMM3; from 0 to 1.0, from 0 to 5.0, or from 0 to 25.0 volume percent DMM4; from 0 to 0.5, from 0 to 1.0, or from 0 to 2.0 volume percent DMM5; or a combination thereof.

In embodiments, a composition according to this disclosure comprises from 5 vol. % to 10 or 20 vol. % of a DMMn oligomer fraction, with less than 1.0 vol. % provided by DMM2, less than 2.0 vol. % provided by DMM5, and the remainder of the volume percentage of the oligomer fraction being provided by DMM3 and/or DMM4.

In embodiments, a herein-disclosed composition further comprises a stabilizer comprising one or more alcohols. Without wishing to be limited by theory, the stabilizer may help stabilize the DMMn oligomers by reacting with formaldehyde to form molecules that will reduce or prevent undesirable reactions in conditions that may be encountered in fuel distribution systems. Such compositions comprising alcohols of certain physical and chemical properties, as described further hereinbelow, in blends with dimethoxymethane oligomers in distillate fuels may have reduced cloud and/or pour points and/or increased fungibility relative to similar compositions absent the alcohol.

Without wishing to be limited by theory, the presence of the alcohol in a composition may promote the formation of hemiformals, thus enhancing product composition properties by reducing formaldehyde content and associated reactions. The alcohol content of compositions according to certain embodiments of this disclosure may also increase the solubility of heavier oligomers (e.g., DMM5+) in the composition.

Alcohol

Alcohols for inclusion in the fuel composition may be selected (e.g., alcohols having a certain boiling point), in embodiments, to provide certain product properties, such as flash point. In embodiments, the alcohol has a boiling point of greater than or equal to 100° C., 150° C., 160° C., 170° C., 180° C., 190° C., 200° C. or 210° C. In embodiments, the alcohol has a boiling point that is in the range of from 95° C. to 220° C., from 95° C. to 170° C., from 110° C. to 220° C., from 110° C. to 170° C., from 95° C. to 110° C., from 110° C. to 170° C., or from 170° C. to 220° C. Alcohols with low water solubility may be effective for increasing fungibility. In embodiments, the alcohol has a low water solubility, as indicated by a water solubility of less than or equal to 25 g/100 mL, 20 g/100 mL, 15 g/100 mL, 10 g/100 mL, 9 g/100 mL, 8 g/100 mL, 7 g/100 mL, 6 g/100 mL, 5 g/100 mL, or 4 g/100 mL at 20° C. In embodiments, the alcohol has a low water solubility, as indicated by a water solubility of less than or equal to 1 g/100 mL, 5 g/100 mL, or 10 g/100 mL at 30° C. In embodiments, the alcohol may be selected from isobutanol, cyclohexanol, 1-octanol, benzyl alcohol, phenylethanol, hexadecanol or a combination thereof. Low water solubility alcohols may provide enhanced fungibility and stabilization of the fuel composition. Alcohols based on renewable feedstocks, such as, without limitation, bio-butanol and/or higher carbon number bio-alcohol(s), may provide for renewable content, low solubility in water and appropriate volatility characteristics. Without wishing to be limited by theory, the stabilizer may enhance stabilization of one or more renewable additive(s) utilized in biodiesel. In embodiments, the stabilizer consists or consists essentially of the one or more alcohols.

In embodiments, a composition produced with all or a portion of the DMM1-2, the DMM2-5, and/or distillate fuel in recovered distillate line 146 of this disclosure comprises less than or equal to 10, 9, 8, 7, 6, 5, 4, 3, 2, or 1 volume percent alcohol. In embodiments, levels of free alcohol in compositions comprising mixtures of alcohol, DMMn, and distillate fuel are less than or less than or equal to 1 volume percent, less than or less than or equal to 3 volume percent, or less than or less than or equal to 5 volume percent. Higher levels of alcohol may also be utilized, in embodiments, provided the increased water phase volume, organic content of the water, product cost, as well as flash point for some alcohols, are acceptable, as such higher alcohol content may be useful for other properties, such as, without limitation, increasing the renewable content of the product composition, e.g., bio-butanol and/or higher carbon number bio-alcohol.

In embodiments, a composition comprising all or a portion of the DMM1-2, the DMM2-5, and/or the distillate fuel in recovered distillate line 146 according to this disclosure comprises a desired volume percentage of an oligomer portion comprising DMMn, and the desired percentage includes less than a desired vol. % DMM2 and/or less than a desired vol. % DMM5, with the remainder of the desired percentage comprising DMM3 and/or DMM4; and a desired volume percentage of alcohol. For example, in embodiments, a composition according to this disclosure comprises 5 vol. % of an oligomer portion comprising DMMn, including less than 1 vol. % DMM2 and/or less than 2 vol. % DMM5, with the remainder of the desired volume percentage comprising DMM3 and/or DMM4; and less than 2 vol. % alcohol (e.g., phenylethanol). In embodiments, a composition comprising all or a portion of the DMM1-2, the DMM2-5, and/or the distillate fuel in recovered distillate line 146 produced according to this disclosure comprises less than or equal to 20 vol. % of an oligomer portion comprising DMMn, including less than 1 vol. % DMM2 and/or less than 2 vol. % DMM5, with the remainder of the desired percentage comprising DMM3 and/or DMM4; and less than 2 vol. % alcohol (e.g., phenylethanol). The remainder of the composition (e.g., greater than 93 vol. % in the first example above, and 78 vol. % in the second example above) may comprise a distillate fuel (e.g., including, without limitation, petroleum diesel, biodiesel, and/or synthetic diesel, with or without typical additives thereof), hydrogenated vegetable oil, or a combination thereof.

In embodiments, a composition according to this disclosure does not comprise an emulsifying agent. For example, in embodiments, a composition according to this disclosure does not comprise oleic acid, ethyl ether, methyl benzoate, acetone, or a combination thereof. In embodiments, a composition according to this disclosure does not comprise DMM6+, i.e., does not comprise oligomers having a chain length n of greater than 5.

A composition produced with all or a portion of the DMM1-2, the DMM2-5, and/or the distillate fuel in recovered distillate line 146 produced according to this disclosure may have an increased cetane content, a reduced pour point, a reduced cloud point, and/or an increased flash point relative to a similar composition. In embodiments, the composition has a flash point of greater than or equal to 55° C., 65C, or 75° C.

In embodiments, a composition produced with all or a portion of the DMM1-2, the DMM2-5, and/or the distillate fuel in recovered distillate line 146 produced according to this disclosure comprises an oligomer portion comprising oligomer(s) DMMn wherein n is greater than 4 (e.g., n is greater than or equal to 5, or 6, and so on). Such a composition may have a cetane content that is greater than or equal to the cetane content of a similar composition in which the oligomer portion does not comprise oligomer(s) wherein n is greater than 4. In embodiments, such a composition has a cloud point and/or a pour point that is within 5, 10, or 15% of the cloud point and/or pour point of a similar composition in which the oligomer portion does not comprise oligomer(s) wherein n is greater than 4.

In embodiments, a composition comprising all or a portion of the DMM1-2, the DMM2-5, and/or the distillate fuel in recovered distillate line 146 produced according to this disclosure comprises a distillate fuel, and less than or less than or equal to a desired maximum volume percent (e.g., less than or equal to 20, 15, 10, 9, 8, 7, 6, 5, 4, 3, 2, or 1 volume percent) of DMMn, and such a composition has a cetane content that is within 5, 10, or 15% of the cetane content of a similar composition comprising greater than the desired maximum volume percent of the oligomer portion. In embodiments, such a composition has a cloud point and/or pour point that is within 5, 10, or 15% of the cloud point and/or pour point, respectively, of a similar composition comprising greater than the desired maximum volume percent of the oligomer portion.

In embodiments, a composition comprising all or a portion of the DMM1-2, the DMM2-5, and/or the distillate fuel in recovered distillate line 146 produced according to this disclosure exhibits a water phase volume increase that is no more than 10, 30, or 50% greater than a water phase volume increase of a similar composition. For example, in embodiments, a composition according to this disclosure comprises an alcohol, and exhibits a water phase volume increase that is no more than 10, 30%, or 50% greater than a water phase volume increase of the same composition absent the alcohol. In embodiments, a composition according to this disclosure comprises an alcohol, and exhibits a reduced free formaldehyde content relative to a free formaldehyde content of the same composition absent the alcohol.

In embodiments, a composition comprising all or a portion of the DMM1-2, the DMM2-5, and/or the distillate fuel in recovered distillate line 146 produced according to this disclosure comprises less than or less than or equal to a desired maximum volume percentage (e.g., 20, 15, 10, 9, 8, 7, 6, 5, 4, 3, 2, or 1 volume percent) of an oligomer portion comprising at least one dimethoxymethane oligomer DMMn, and exhibits a water phase volume increase that is at least 50, 30, or 10% less than a water phase volume increase of a similar composition comprising greater than the maximum desired volume percent of the oligomer portion.

Features

As DMM2-5 provides a broad oligomer distribution that meets flash point and cloud point specifications for fuels, a system and method as disclosed herein, which enables the production of DMM2-5 (along with DMM1-2, and DMM5+) can be utilized to provide DMM oligomers and oligomer fractions for incorporation into fuels. The DMM2-5 can be tailored as described herein to contain certain amounts of DMM2 and/or DMM5 (e.g., to provide DMMn product comprising less than a desired amount of DMM2 and/or DMM5). The utilization of alcohol blends and/or distillate diluent throughout a two-step DMMn distillation, as described herein, may provide for minimization of free formaldehyde and/or deposition of heavier oligomer mixtures throughout the DMA/In distillation, respectively. Utilization of free formaldehyde as a formaldehyde source for the production of DMMn, as per this disclosure, may provide for a more economical process (e.g., relative to processes that utilize more expensive sources of formaldehyde, such as trioxane or paraformaldehyde). Production of a formaldehyde source comprising free formaldehyde and DMM1, as per this disclosure, may improve mixing of DMM1 and anhydrous formaldehyde for the subsequent production of DMMn therefrom, and may enhance safety by eliminating the presence of pure or substantially pure anhydrous formaldehyde within the system/process.

The following example merely illustrates the system and method of this disclosure. Those skilled in the art will recognize many variations that are within the spirit of this disclosure and the scope of the claims.

EXAMPLE

Example 1

An anhydrous formaldehyde source 102' containing anhydrous formaldehyde and DMM1 is produced as per the embodiment of FIG. 3. As per the embodiment of FIG. 2, a formaldehyde source in formaldehyde source inlet line 102 is utilized to produce a purified DMM2-5 stream in purified DMM2-5 line 142, DMM1-2 extracted as an overhead from first distillation column 120 via first distillation column overhead line 125, and heavy oligomer stream comprising DMM5+ removed from extractor 145 via heavy oligomer outlet line 147. Diesel for external blending in line 122B is combined with DMM2-5 product in DMM2-5 line 142 at a blending terminal, which may be located outside of DMMn production system 100 and is represented by mixer M7. The final blend in DMMn product line 148 comprises approximately 4.7% DMMn. Flow rates for the various streams depicted in FIGS. 2 and 3 and described hereinabove are provided in Table 1.

TABLE 1

Flow Rates of Various Streams in Example 1

|  | Flow Rate (lb/h (kg/h)) |
|---|---|
| Line Number in FIG. 2 | |
| 101 | 13,238 (6,005) |
| 102 | 11,492 (5,213) |
| 121A | 911 (413) |
| 121B | 911 (413) |
| 122A | 3,976 (1,803) |
| 122B | 500,475 (227,011) |
| 123 | 45,562 (20,667) |
| 125 | 15,035 (6,820) |
| 127A | 12,319 (5,588) |
| 127B | 12,319 (5,588) |
| 126A' | 2,944 (1,335) |
| 126B' | 2,944 (1,335) |
| 142 | 27,583 (12,511) |
| 143 | 5,888 (2,671) |
| 144 | 5,888 (2,671) |
| 147 | 8,803 (3,993) |
| 148 | 528,058 (239,523) |
| Line Number in FIG. 3 | |
| 102' | 13,492 (6,120) |
| 151 | 383 (174) |
| 152 | 22,981 (10,424) |
| 153 | 2000 (907) |
| 161 | 61,356 (27,831) |
| 171 | 11,074 (5,023) |
| 181 | 414 (188) |
| 193 | 384 (174) |
| 194 | 37,992 (17,233) |

ADDITIONAL DISCLOSURE

The particular embodiments disclosed above are merely illustrative, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, each range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and unambiguously defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method of producing dimethoxymethane oligomers (DMMn), the method comprising: reacting a formaldehyde source and dimethoxymethane monomer (DMM1) in the presence of an acidic catalyst to produce a reaction effluent comprising DMMn and unreacted DMM1; and separating, from the reaction effluent, DMM1-2 including unreacted DMM1 and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof, wherein the separating comprises distillation in the presence of at least one alcohol, a distillate fuel, or both.

B: A system for producing dimethoxymethane oligomers (DMMn), the system comprising: a DMMn reactor configured for reacting a formaldehyde source and dimethoxymethane monomer (DMM1) in the presence of an acidic catalyst to produce a reactor effluent comprising DMMn and unreacted DMM1; a first distillation column configured to separate, from the reactor effluent, a first distillation column overhead comprising DMM1-2 including unreacted DMM1 and DMMn having a chain length n equal to 2 (DMM2) from a first distillation column bottoms comprising DMMn wherein n is greater than or equal to 2 (DMM2+); and a second distillation column configured to separate, from the first distillation column bottoms, a second distillation column overhead comprising dimethoxymethane oligomers having a chain length n in the range of from 2-5 (DMM2-5) from a second distillation column bottoms comprising dimethoxymethane oligomers having a chain length n of ≥5 (DMM5+), wherein the first distillation column, the second distillation column, or both are configured for operation in the presence of at least one alcohol, a distillate fuel, or both.

C: A method of producing dimethoxymethane oligomers (DMMn), the method comprising: separating, from a DMMn reaction effluent, DMM1-2 comprising unreacted dimethoxymethane monomer (DMM1) and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof, wherein the separating comprises distillation in the presence of at least one alcohol, a distillate fuel, or both.

D: A method of producing dimethoxymethane oligomers (DMMn), the method comprising: producing a feed comprising anhydrous formaldehyde and dimethoxymethane monomer (DMM1) by: reacting aqueous formaldehyde with an alcohol to produce a reaction effluent comprising hemiformal; decomposing the hemiformal to produce the anhydrous formaldehyde; and subjecting the anhydrous formaldehyde to distillation in the presence of DMM1 to separate a heavy stream comprising unreacted alcohol from the feed comprising anhydrous formaldehyde and DMM1; and reacting the feed comprising anhydrous formaldehyde and DMM1 in the presence of an acidic catalyst to produce a reaction effluent comprising DMMn.

E: A system for producing dimethoxymethane oligomers (DMMn), the system comprising: a first distillation column configured to separate, from a reactor effluent comprising DMMn, a first distillation column overhead comprising DMM1-2 including dimethoxymethane monomer (DMM1) and DMMn having a chain length n equal to 2 (DMM2) from a first distillation column bottoms comprising DMMn wherein n is greater than or equal to 2 (DMM2+); and a second distillation column configured to separate, from the first distillation column bottoms, a second distillation column overhead comprising dimethoxymethane oligomers having a chain length n in the range of from 2-5 (DMM2-5) from a second distillation column bottoms comprising dimethoxymethane oligomers having a chain length n of ≥5 (DMM5+), wherein the first distillation column, the second distillation column, or both are configured for operation in the presence of at least one alcohol, a distillate fuel, or both.

F: A method of producing dimethoxymethane oligomers (DMMn), the method comprising: producing anhydrous formaldehyde by: reacting aqueous formaldehyde with an alcohol to produce a reaction effluent comprising hemiformal; decanting to separate an aqueous phase comprising water from an organic phase comprising the hemiformal; separating water from the organic phase via membrane filtration, another separation, or a combination thereof, to provide an anhydrous hemiformal; and decomposing the anhydrous hemiformal to produce the anhydrous formaldehyde, subjecting the anhydrous formaldehyde to distillation in the presence of dimethoxymethane monomer (DMM1) to separate a heavy stream comprising unreacted alcohol from an anhydrous formaldehyde source containing anhydrous formaldehyde and DMM1, reacting the anhydrous formaldehyde and DMM1 in the presence of an acidic catalyst to produce a reaction effluent comprising DMMn and unreacted DMM1; and separating, from the reaction effluent, DMM1-2 including unreacted DMM1 and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof, wherein the separating, from the reaction effluent, comprises distillation in the presence of at least one alcohol, a distillate fuel, or both.

Each of embodiments A, B, C, D, E and F may have one or more of the following additional elements: Element 1: wherein the at least one alcohol comprises a low volatility alcohol, as evidenced by a boiling point of greater than or equal to 100° C., 150° C., 160° C., 170° C., 180° C., 190° C., 200° C. or 210°, a boiling point in the range of from 95° C. to 220° C., from 95° C. to 170° C., from 110° C. to 220° C., from 110° C. to 170° C., from 95° C. to 110° C., from 110° C. to 170° C., or from 170° C. to 220° C., or a combination thereof. Element 2: wherein the at least one alcohol has a low water solubility, as indicated by a water solubility of less than or equal to 25 g/100 mL, 20 g/100 mL, 15 g/100 mL, 10 g/100 mL, 9 g/100 mL, 8 g/100 mL, 7 g/100 mL, 6 g/100 mL, 5 g/100 mL, or 4 g/100 mL at 20° C., less than or equal to 1 g/100 mL, 5 g/100 mL, or 10 g/100 mL at 30° C., or a combination thereof. Element 3: wherein the at least one alcohol is selected from methanol, ethanol, propanol, isobutanol, cyclohexanol, octanol, benzyl alcohol, phenylethanol, hexadecanol, or a combination thereof. Element 4: wherein the at least one alcohol comprises an alcohol produced from a renewable feedstock, such as, without limitation, bio-butanol and/or higher carbon number bio-alcohol(s). Element 5: wherein the at least one alcohol comprises a blend of at least two alcohols, at least two alcohols introduced at at least two different places relative to the distillation, or both. Element 6: wherein the at least two alcohols comprise a first alcohol and a second alcohol having a different volatility from that of the first alcohol. Element 7: wherein the at least one alcohol reacts with free formaldehyde, thus decreasing the concentration thereof. Element 8: wherein the distillate fuel comprises diesel. Element 9: wherein the diesel comprises renewable diesel, such as biodiesel. Element 10: wherein the distillate fuel serves as a diluent to reduce the viscosity and prevent deposition of heavier (e.g., n≥5 or DMM5+) oligomers during the separating. Element 11: further comprising recycling at least a portion of the DMM1-2 to the reacting of the formaldehyde source and DMM1 in the presence of the acidic catalyst to produce the reaction effluent comprising DMMn. Element 12: wherein the separating comprises subjecting at least a portion of the reaction effluent comprising DMMn to a first distillation to separate a first distillation overhead comprising DMM1-2 and a first distillation bottoms comprising DMMn wherein n is greater than or equal to 2 (DMM2+). Element 13: wherein subjecting the at least a portion of the reaction effluent to the first distillation comprises subjecting the at least a portion of the reaction effluent to distillation in the presence of the at least one alcohol, the distillate fuel, or both. Element 14: wherein a feed to the first distillation comprises or wherein the first distillation column is configured for operation with a first distillation column feed comprising from 45 to 100, from 45 to 90, from 45 to 50, from 90 to 100, from 80 to 100, from 70 to 100 weight percent (wt %) of the reactor/reaction effluent, from 0.1 to 10.0, from 0.5 to 10.0, from 0.5 to 6.0, from 0.5 to 2.0, from 0.1 to 3.0, or from 0.1 to 1.5 wt % of the at least one alcohol, from 0 to 60, from 0 to 50, from 0 to 20, from 0 to 30, or from 10 to 50 wt % of the distillate fuel, or a combination thereof. Element 15: further comprising subjecting the first distillation bottoms comprising DMMn to a second distillation to produce a second distillation overhead comprising DMM2-5 and a second distillation bottoms comprising DMM5+. Element 16: wherein subjecting the at least a portion of the reaction effluent to the first distillation comprises subjecting the at least a portion of the reaction effluent to distillation in the presence of the at least one alcohol, the distillate fuel, or both, and wherein the at least one alcohol comprises a blend of at least two alcohols, including a first alcohol and a second alcohol having a boiling point greater than that of the first alcohol, whereby the first distillation bottoms comprises at least a portion of the second alcohol. Element 17: further comprising recycling at least a portion of the second distillation bottoms to the second distillation. Element 18: wherein the at least a portion of the second distillation bottoms is recycled to the second distillation via combination with the first distillation bottoms to provide a second distillation feed. Element 19: wherein a feed to the second distillation comprises or the second distillation column is configured for operation with a second distillation column feed comprising from 80 to 100, from 90 to 100, or from 95 to 100 weight percent (wt %) of the first distillation bottoms, from 0 to 20, from 0 to 10, or from 0 to 5 wt % of the recycled second distillation bottoms, or a combination thereof. Element 20: further comprising combining the distillate fuel with the second distillation overhead. Element 21: further comprising removing acid, base, water, formaldehyde, or a combination thereof from the second distillation overhead to provide a purified DMM2-5 stream. Element 22: wherein removing acid, base, water, formaldehyde, or a combination thereof from the second distillation overhead comprises cooling, filtration, contact with an adsorbent, or a combination thereof. Element 23: wherein the adsorbent comprises calcium carbonate, hydroxide, alumina, activated carbon, adsorbent clay, or another industrial adsorbent effective for adsorbing acid, base, water, aldehyde, or a combination thereof. Element 24: further comprising subjecting at least a portion of the second distillation bottoms to extraction with an extractant, chilling, centrifugation, other filtration, or a combination thereof to produce a heavy oligomer product comprising DMM5+ and a recovered stream comprising the distillate fuel. Element 25: further comprising removing acid, base, water, formaldehyde, or a combination thereof from the second distillation overhead to provide a purified DMM2-5 stream, removing acid, base, water, or a combination thereof from the recovered stream to provide a purified recovered stream, or both; and combining the purified DMM2-5 stream with the recovered stream, the purified recovered stream, or both to yield a DMMn product. Element 26: wherein the extractant comprises an alcohol, water, or both. Element 27: wherein the extractant comprises an alcohol selected from methanol, ethanol, propanol, isobutanol, cyclohexanol, octanol, benzyl alcohol, phenylethanol, hexadecanol, or a combination thereof. Element 28: wherein the extractant comprises at least one alcohol utilized in the separating, from the reaction effluent, DMM1-2, DMM2-5, DMM5+, or a combination thereof. Element 29: further comprising removing water, alcohol, or both from the heavy oligomer product comprising DMM5+, and recycling the heavy oligomer product from which the water, alcohol, or both has been removed to a level suitable for recycling. Element 30: wherein the heavy oligomer product from which the water, the alcohol, or both has been removed is recycled to the reacting of the formaldehyde source and the DMM1 in the presence of the acidic catalyst to produce the reaction effluent comprising DMMn, the first distillation, the second distillation, or a combination thereof. Element 31: wherein the heavy oligomer product from which the water, the alcohol, or both has been removed is recycled to the reacting of the formaldehyde source and the DMM1 such that the reacting is performed in the presence of less than or equal to 5, 1, or 0.1 wt % water, less than or equal to 5, 1, or 0.1 wt % alcohol, or less than or equal to 5, 1, or 0.1 wt % water and less than or equal to 5, 1, or 0.1 wt % alcohol. Element 32: further comprising: producing anhydrous formaldehyde as the formaldehyde source by: reacting aqueous formaldehyde with an alcohol to produce a reaction effluent comprising hemiformal; and decomposing the hemiformal to produce the anhydrous formaldehyde. Element 33: wherein decomposing comprises heating to a temperature of greater than or equal to 125° C., 150° C., or 175° C. Element 34: wherein the alcohol reacted with the aqueous formaldehyde comprises a low solubility alcohol, as indicated by a water solubility of less than or equal to 25 g/100 mL, 20 g/100 mL, 15 g/100 mL, 10 g/100 mL, 9 g/100 mL, 8 g/100 mL, 7 g/100 mL, 6 g/100 mL, 5 g/100 mL, or 4 g/100 mL at 20° C., less than or equal to 1 g/100 mL, 5 g/100 mL, or 10 g/100 mL at 30° C., or a combination thereof. Element 35: wherein the alcohol reacted with the aqueous formaldehyde is selected from cyclohexanol, isobutanol, phenylethanol, or a combination thereof. Element 36: further comprising removing water from the reaction effluent comprising hemiformal prior to decomposing the hemiformal to produce the anhydrous formaldehyde. Element 37: wherein removing water from the reaction effluent comprising hemiformal further comprises decanting, filtration, adsorption, absorption, or a combination thereof. Element 38: wherein removing water from the reaction effluent comprising hemiformal (further) comprises: decanting to separate an aqueous phase comprising water from an organic phase comprising the hemiformal; and separating water from the organic phase via membrane filtration, another separation, or a combination thereof, to provide an (the) anhydrous hemiformal. Element 39: further comprising subjecting the anhydrous formaldehyde to distillation to separate a heavy stream comprising unreacted alcohol from the anhydrous formaldehyde. Element 40: wherein the subjecting of the anhydrous formaldehyde to distillation to separate a heavy stream comprising unreacted alcohol from the anhydrous formaldehyde further comprises distillation in the presence of DMM1, thus providing an anhydrous formaldehyde source containing anhydrous formaldehyde and DMM1. Element 41: wherein the presence of DMM1 in the anhydrous formaldehyde source improves the mixing of the anhydrous formaldehyde and the DMM1 prior to the reacting of the formaldehyde source and the DMM1 in the presence of the acidic catalyst to produce the reaction effluent comprising DMMn, enhances safety relative to the use of a pure or substantially pure anhydrous formaldehyde source, or both. Element 42: wherein the anhydrous formaldehyde source comprises at least 40, 70, or 100 wt % anhydrous formaldehyde, at least 0, 30, or 60 wt % DMM1, less than or equal to 0.1, 1.0, or 2.0 wt % water, or a combination thereof. Element 43: wherein reacting the formaldehyde source and DMM1 in the presence of the acidic catalyst comprises introducing the anhydrous formaldehyde source comprising anhydrous formaldehyde and DMM1 into a DMMn production reactor, wherein the anhydrous formaldehyde source is contacted with the acidic catalyst. Element 44: further comprising recycling at least a portion of the heavy stream comprising unreacted alcohol to the producing of the anhydrous formaldehyde as the formaldehyde source by reacting aqueous formaldehyde with the alcohol to produce the reaction effluent comprising hemiformal. Element 45: wherein the reacting of the formaldehyde source and DMM1 in the presence of the acidic catalyst to produce the reaction effluent comprising DMMn is effected or wherein the DMMn reactor is operable at a temperature in the range of from 40° C. to 100° C., from 40° C. to 80° C., or from 40° C. to 60° C., a pressure in the range of from 100 kPa to 4000 kPa, from 100 kPa to 500 kPa, or from 100 kPa to 300 kPa, or a combination thereof. Element 46: wherein the formaldehyde source is selected from formaldehyde, trioxane, paraformaldehyde, or combinations thereof. Element 47: wherein the formaldehyde source comprises formaldehyde containing a water level such that the reacting of the formaldehyde source and DMM1 is effected in the presence of less than or equal to 0.1, 1.0, or 2.0 wt % water. Element 48: wherein the formaldehyde source comprises anhydrous formaldehyde containing a water level such that the reacting of the formaldehyde source and DMM1 is effected in the presence of less than or equal to 0.1, 1.0, or 2.0 wt % water. Element 49: further comprising a removal step for removing trace acid, base, or both. Element 50: wherein the removal step comprises removing acid, base, or both from the reaction effluent comprising DMMn (i) downstream of a DMMn production reactor in which the reaction effluent comprising DMMn is produced, (ii) upstream of the separating, (iii) between separating of DMM1-2 and separating of DMM2-5 from the reaction effluent, (iv) subsequent separating of DMM2-5 from the reaction effluent comprising DMMn, or (v) a combination thereof. Element 51: wherein the reacting of the formaldehyde source and the DMM1 is effected in the presence of less than or equal to 5, 1, or 0.1 wt % water, less than or equal to 5, 1, or 0.1 wt % alcohol, or less than or equal to 5, 1, or 0.1 wt % water and less than or equal to 5, 1, or 0.1 wt % alcohol. Element 52: further comprising producing at least a portion of the DMM1 by reacting aqueous formaldehyde with methanol. Element 53: wherein the formaldehyde source comprises or is produced from aqueous formaldehyde, wherein the at least one alcohol comprises methanol, and wherein the method further comprises producing at least a portion of the aqueous formaldehyde via oxidation of methanol. Element 54: wherein the formaldehyde source, the DMM1, or both is produced at least in part from a renewable source, such as, without limitation methanol from synthesis gas which is derived from gasification of plastic waste, municipal solid waste, bio-waste, agricultural crops, or a combination thereof. Element 55: further comprising removing deposited paraformaldehyde and associated solids by heating, and reacting any free formaldehyde generated with the at least one alcohol to reduce a free formaldehyde content. Element 56: further comprising utilizing the DMM1-2, the DMM2-5, the DMM5+, the recovered stream comprising the distillate fuel, or a combination thereof in a fuel application, a chemical application, a polymer application, or a combination thereof. Element 57: wherein the acidic catalyst comprises AMBERLYST® 15, ZSM-5, AMBERLYST® 46, other acidic zeolites, other macroreticular structures with H+ functionality, or a combination thereof. Element 58: further comprising flashing the reaction effluent comprising DMMn to remove at least one component therefrom prior to the separating, from the reaction effluent, of DMM1-2, DMM2-5, DMM5+, or a combination thereof. Element 59: wherein the at least one component comprises water, unreacted formaldehyde source, DMM1, DMM2, or a combination thereof. Element 60: further comprising recycling at least a portion of the at least one component to the reacting of the formaldehyde source and DMM1 in the presence of the acidic catalyst to produce the reaction effluent comprising DMMn.

Element 61: further comprising a recycle line whereby at least a portion of the DMM1-2 can be introduced into the DMMn reactor. Element 62: further comprising a recycle line whereby at least a portion of the second distillation column bottoms can be recycled to the second distillation column. Element 63: wherein the second distillation column is configured for operation with from a second distillation column feed comprising from 80 to 100, from 90 to 100, or from 95 to 100 weight percent (wt %) of the first distillation column bottoms, from 0 to 20, from 0 to 10, or from 0 to 5 wt % of the recycled second distillation column bottoms, or a combination thereof. Element 64: comprising an inlet line configured for the introduction of the at least one alcohol into the first distillation column, an inlet line configured for the introduction of the at least one alcohol into the second distillation column, an inlet line configured for the introduction of the distillate fuel into the first distillation column, an inlet line configured for the introduction of the distillate fuel into the second distillation column, or a combination thereof. Element 65: wherein the inlet line is configured for the introduction of the at least one alcohol, the distillate fuel, or both into a top portion, above a feed tray, of the first distillation column, the second distillation column, or both. Element 66: wherein the reactor effluent is introduced into the first distillation column at a mid-point thereof. Element 67: wherein the first distillation column bottoms is introduced into the second distillation column at a point within an upper section or half thereof. Element 68: wherein the at least one alcohol comprises a blend of at least two alcohols, including a first alcohol and a second alcohol having a boiling point greater than that of the first alcohol, and wherein the first distillation bottoms comprises at least a portion of the second alcohol. Element 69: further comprising an inlet line for combining the distillate fuel with the second distillation column overhead. Element 70: further comprising removal apparatus configured for the removal of acid, base, water, formaldehyde, or a combination thereof from the second distillation column overhead to provide a purified DMM2-5 stream. Element 71: wherein the removal apparatus comprises a cooler, a filter, an adsorbent, or a combination thereof. Element 72: further comprising an extractor, a chiller, a centrifuge, other separator, or a combination thereof configured to produce, from at least a portion of the second distillation column bottoms, via extraction with an extractant, chilling, centrifugation, other filtration, or a combination thereof, respectively, a heavy oligomer product comprising DMM5+ and a recovered stream comprising the distillate fuel. Element 73: further comprising removal apparatus configured for the removal of acid, base, water, formaldehyde, or a combination thereof from the second distillation column overhead, the recovered stream, or both to provide a purified DMM2-5 stream, a purified recovered stream, or both, and one or more lines configured to combine the purified DMM2-5 stream with the recovered stream, the purified recovered stream, or both to yield a DMMn product. Element 74: wherein the extractant comprises at least one of the at least one alcohols in the presence of which the first distillation column, the second distillation column, or both are operated. Element 75: further comprising separation apparatus configured to remove water, alcohol, or both from the heavy oligomer product comprising DMM5+, and a heavy oligomer recycle line configured to recycle at least a portion of the heavy oligomer product from which the water, alcohol, or both has been removed, optionally with the heavy oligomer product being depolymerized in the presence of acidic species prior to recycling. Element 76: wherein the heavy oligomer recycle line is configured to recycle at least a portion of the heavy oligomer product from which the water, the alcohol, or both has been removed to the DMMn reactor, the first distillation column, the second distillation column, or a combination thereof. Element 77: further comprising: a hemiacetal reactor configured for the reaction of aqueous formaldehyde with an alcohol to produce a hemiacetal reactor effluent comprising hemiformal; and a decomposition vessel configured to decompose the hemiformal to produce anhydrous formaldehyde. Element 78: wherein the decomposition vessel is operable to heat the hemiformal to a temperature of greater than or equal to 125° C., 150° C., or 175° C. Element 79: further comprising water removal apparatus configured to remove water from the hemiacetal reactor effluent comprising hemiformal upstream of the decomposition vessel. Element 80: wherein the water removal apparatus comprises one or more units selected from decanters, filtration units, adsorbers, absorbers, or a combination thereof. Element 81: wherein the water removal apparatus comprises: a decanter configured to separate an aqueous phase comprising water from an organic phase comprising the hemiformal; and a separator configured to separate water from the organic phase via membrane filtration, another separation, or a combination thereof, to provide an anhydrous hemiformal. Element 82: further comprising a distillation column configured to subject the anhydrous formaldehyde to distillation to separate a heavy stream comprising unreacted alcohol from the anhydrous formaldehyde. Element 83: further comprising a DMM1 inlet line configured to introduce DMM1 into the distillation column configured to subject the anhydrous formaldehyde to distillation to separate the heavy stream comprising unreacted alcohol from an anhydrous formaldehyde source containing anhydrous formaldehyde and DMM1. Element 84: further comprising a recycle line whereby at least a portion of the heavy stream comprising unreacted alcohol can be recycled to the hemiacetal reactor. Element 85: further comprising a removal apparatus configured for removing trace acid, base, or both. Element 86: wherein the removal apparatus is located downstream of the DMMn reactor, upstream of the first distillation column, downstream of the second distillation column, between the DMMn reactor and the first distillation column, between the first distillation column and the second distillation column, or a combination thereof. Element 87: further comprising a flash vessel configured to remove at least one component from the reactor effluent comprising DMMn upstream of the first distillation column. Element 88: further comprising a recycle line configured to recycle at least a portion of the at least one component to the DMMn reactor. Element 89: wherein the feed comprising anhydrous formaldehyde and DMM1 comprises at least 40, 70, or 100 wt % anhydrous formaldehyde, at least 0, 30, or 60 wt % DMM1, less than or equal to 0.1, 1.0, or 2.0 wt % water, or a combination thereof. Element 90: further comprising a DMMn reactor configured for reacting a formaldehyde source and dimethoxymethane monomer (DMM1) in the presence of an acidic catalyst to produce the reactor effluent comprising DMMn. Element 91: further comprising a distillation column configured to subject a feed stream comprising anhydrous formaldehyde and an excess of an alcohol utilized in the production of the anhydrous formaldehyde to distillation in the presence of DMM1 to provide a heavy stream comprising the excess alcohol and an anhydrous formaldehyde stream comprising DMM1, wherein the formaldehyde source comprises the anhydrous formaldehyde stream comprising DMM1. Element 92: further comprising an extractor configured to separate, from the second distillation column bottoms via extraction with an extractant, a heavy oligomer product comprising DMM5+ and a recovered stream comprising the distillate fuel.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A method of producing dimethoxymethane oligomers (DMMn), the method comprising:
    reacting a formaldehyde source and dimethoxymethane monomer (DMM1) in the presence of an acidic zeolite catalyst to produce a reaction effluent comprising DMMn and unreacted DMM1; and
    separating, from the reaction effluent, DMM1-2 including unreacted DMM1 and DMMn having a chain length n equal to 2 (DMM2), dimethoxymethane oligomers having a chain length n in the range of from 2-5 (DMM2-5), dimethoxymethane oligomers having a chain length n of ≥5 (DMM5+), or a combination thereof,
    wherein the separating comprises distillation in the presence of at least one alcohol, a distillate fuel, or both, wherein the separating comprises subjecting at least a portion of the reaction effluent comprising DMMn to a first distillation to separate a first distillation overhead comprising DMM1-2 and a first distillation bottoms comprising DMMn wherein n is greater than or equal to 2 (DMM2+); wherein the method further comprising subjecting the first distillation bottoms comprising DMMn to a second distillation to produce a second distillation overhead comprising DMM2-5 and a second distillation bottoms comprising DMM5+; wherein the reaction effluent comprises:
    greater than 0 to less than 1,0 volume percent of DMM2;
    greater than 0 to less than 25 volume percent of DMM3;
    greater than 0 to less than 25 volume percent of DMM4; and
    greater than 0 to less than 2,0 volume percent of DMM5.

2. The method of claim 1, wherein subjecting the at least a portion of the reaction effluent to the first distillation comprises subjecting the at least a portion of the reaction effluent to distillation in the presence of the at least one alcohol, the distillate fuel, or both.

3. The method of claim 2, wherein a feed to the first distillation comprises from 45 to 90 weight percent (wt %) of the reaction effluent, from 0.1 to 10.0 wt % of the at least one alcohol, from 0 to 60 wt % of the distillate fuel, or a combination thereof.

4. The method of claim 1, wherein subjecting the at least a portion of the reaction effluent to the first distillation comprises subjecting the at least a portion of the reaction effluent to distillation in the presence of the at least one alcohol, the distillate fuel, or both, and wherein the at least one alcohol comprises a blend of at least two alcohols, including a first alcohol and a second alcohol having a boiling point greater than that of the first alcohol, whereby the first distillation bottoms comprises at least a portion of the second alcohol.

5. The method of claim 1, further comprising:
    producing anhydrous formaldehyde as the formaldehyde source by:
        reacting aqueous formaldehyde with an alcohol to produce a reaction effluent comprising hemiformal; and
        decomposing the hemiformal to produce the anhydrous formaldehyde.

6. The method of claim 5 further comprising removing water from the reaction effluent comprising hemiformal prior to decomposing the hemiformal, wherein removing water from the reaction effluent comprising hemiformal further comprises decanting, filtration, adsorption, absorption, or a combination thereof.

7. The method of claim 5 further comprising subjecting the anhydrous formaldehyde to distillation in the presence of DMM1 to separate a heavy stream comprising unreacted alcohol from an anhydrous formaldehyde source containing anhydrous formaldehyde and DMM1.

8. The method of claim 7, wherein reacting the formaldehyde source and DMM1 in the presence of the acidic zeolite catalyst comprises introducing the anhydrous formaldehyde source comprising anhydrous formaldehyde and DMM1 into a DMMn production reactor, wherein the anhydrous formaldehyde source is contacted with the acidic zeolite catalyst.

* * * * *

UNITED STATES PATENT AND TRADEMARK OFFICE
CERTIFICATE OF CORRECTION

PATENT NO. : 10,988,564 B2  
APPLICATION NO. : 16/297254  
DATED : April 27, 2021  
INVENTOR(S) : Waguespack et al.

Page 1 of 1

It is certified that error appears in the above-identified patent and that said Letters Patent is hereby corrected as shown below:

In the Specification

In Column 10, Line 41, delete "126W," and insert -- 126B", --, therefor  
In Column 20, Line 53, delete "DMA/In" and insert -- DMMn --, therefor Signed and Sealed this  
Twenty-fourth Day of January, 2023

Katherine Kelly Vidal  
*Director of the United States Patent and Trademark Office*